US011886858B2

(12) United States Patent
Housel et al.

(10) Patent No.: US 11,886,858 B2
(45) Date of Patent: *Jan. 30, 2024

(54) MEDICAL MONITORING HUB

(71) Applicant: Masimo Corporation, Irvine, CA (US)

(72) Inventors: Peter Scott Housel, Irvine, CA (US); Bilal Muhsin, San Clemente, CA (US)

(73) Assignee: Masimo Corporation, Irvine, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/443,384

(22) Filed: Jul. 26, 2021

(65) Prior Publication Data

US 2022/0004376 A1 Jan. 6, 2022

Related U.S. Application Data

(63) Continuation of application No. 15/962,961, filed on Apr. 25, 2018, now Pat. No. 11,086,609, which is a (Continued)

(51) Int. Cl.
*G06F 8/65* (2018.01)
*G06F 9/4401* (2018.01)
(Continued)

(52) U.S. Cl.
CPC .............. *G06F 8/65* (2013.01); *G06F 9/4401* (2013.01); *G06F 11/1417* (2013.01);
(Continued)

(58) Field of Classification Search
None
See application file for complete search history.

(56) References Cited

U.S. PATENT DOCUMENTS

| 4,960,128 A | 10/1990 | Gordon et al. |
| 4,964,408 A | 10/1990 | Hink et al. |
| (Continued) | | |

FOREIGN PATENT DOCUMENTS

| JP | 2000-166878 | 6/2000 |
| WO | WO 2016/138240 | 9/2016 |
| (Continued) | | |

OTHER PUBLICATIONS

Wahler, Michael et al., Disruption-free Software Updates in Automation Systems, 2014, https://ieeexplore.ieee.org/stamp/stamp.jsp?tp=&arnumber=7005075 (last visited Apr. 5, 2021) (Year: 2014).*

(Continued)

*Primary Examiner* — Jonathon A. Szumny
*Assistant Examiner* — Nicholas Akogyeram, II
(74) *Attorney, Agent, or Firm* — Knobbe, Martens, Olson & Bear, LLP

(57) ABSTRACT

A patient monitoring system includes a physiological sensor to sense light after it has passed through tissue of a patient and generate a signal indicative a physiological parameters in response to the sensed light, and a patient monitoring device in communication with the physiological sensor to receive the signal and determine measurements of the physiological parameters from the received signal. The patient monitoring device includes a processor and memory having multiple system images. The patient monitoring device downloads an image upgrade to one system image that the not latest used or tested system image. The patient monitoring device boots the processor from the system image that includes the image upgrade. If the upgraded system image fails, the patient monitoring device boots the processor from another system image of the multiple system images. The patient monitoring device repairs the failed system image.

20 Claims, 29 Drawing Sheets

Related U.S. Application Data continuation-in-part of application No. 15/903,845, filed on Feb. 23, 2018, now Pat. No. 10,956,950.

(60) Provisional application No. 62/560,008, filed on Sep. 18, 2017, provisional application No. 62/463,461, filed on Feb. 24, 2017, provisional application No. 62/463,490, filed on Feb. 24, 2017.

(51) Int. Cl.
*G16H 40/40* (2018.01)
*G16H 40/67* (2018.01)
*G06F 11/14* (2006.01)
*G16H 30/20* (2018.01)
*G16H 40/20* (2018.01)
*G06F 8/61* (2018.01)

(52) U.S. Cl.
CPC ......... *G06F 11/1433* (2013.01); *G16H 30/20* (2018.01); *G16H 40/20* (2018.01); *G16H 40/40* (2018.01); *G16H 40/67* (2018.01); *G06F 8/63* (2013.01)

(56) References Cited

U.S. PATENT DOCUMENTS

| | | |
|---|---|---|
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |

(56) References Cited

U.S. PATENT DOCUMENTS

| | | |
|---|---|---|
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |

(56) References Cited

U.S. PATENT DOCUMENTS

| | | |
|---|---|---|
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,217,795 B2 * | 7/2012 | Carlton-Foss ....... A61B 5/0024 340/4.1 |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |

(56) References Cited

U.S. PATENT DOCUMENTS

| | | |
|---|---|---|
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,380,586 B2 | 6/2016 | Wang |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |

(56) References Cited

U.S. PATENT DOCUMENTS

| | | |
|---|---|---|
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |

(56) References Cited

U.S. PATENT DOCUMENTS

| | | |
|---|---|---|
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,086,609 B2 | 8/2021 | Housel et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| 11,678,829 B2 | 6/2023 | Al-Ali et al. |
| 11,684,296 B2 | 6/2023 | Vo et al. |
| 11,692,934 B2 | 7/2023 | Normand et al. |
| 11,701,043 B2 | 7/2023 | Al-Ali et al. |
| 11,721,105 B2 | 8/2023 | Ranasinghe et al. |
| 2001/0034477 A1 | 10/2001 | Mansfield et al. |
| 2001/0039483 A1 | 11/2001 | Brand et al. |
| 2001/0041831 A1 | 11/2001 | Starkweather et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0129518 A1 | 6/2008 | Carlton-Foss |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0119330 A1 | 5/2009 | Sampath et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |

(56) References Cited

U.S. PATENT DOCUMENTS

| | | |
|---|---|---|
| 2011/0208015 A1 | 8/2011 | Welch et al. |
| 2011/0214021 A1* | 9/2011 | Vidal ................. G06F 11/0715 |
| | | 714/E11.144 |
| 2011/0230733 A1 | 9/2011 | Al-Ali |
| 2011/0289497 A1 | 11/2011 | Kiaie et al. |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Aï |
| 2013/0023775 A1 | 1/2013 | Lamego et al. |
| 2013/0036328 A1 | 2/2013 | Mutisya et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0296672 A1 | 11/2013 | O'Neil et al. |
| 2013/0311926 A1 | 11/2013 | Keegan et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0283011 A1 | 9/2014 | Orona et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0073965 A1 | 3/2016 | Addison et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0253471 A1* | 9/2016 | Volpe ........................ G06F 8/65 |
| | | 607/5 |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0311891 A1 | 11/2017 | Kiani et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |

(56) References Cited

U.S. PATENT DOCUMENTS

| | | |
|---|---|---|
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |

FOREIGN PATENT DOCUMENTS

| | | | | |
|---|---|---|---|---|
| WO | WO-2016138240 A1 | * | 9/2016 | ............. G16H 40/40 |
| WO | WO 2018/156648 | | 8/2018 | |

OTHER PUBLICATIONS

International Search Report and Written Opinion received in PCT Application No. PCT/US2018/019042, dated May 21, 2018 in 10 pages.

Wahler et al., "Disruption-Free Software Updates in Automation Systems", 2014 IEEE Emerging Technology and Factory Automation (ETFA), 2014, pp. 8.

* cited by examiner

DATABASE FIELDS FOR HOSPITAL CONFIGURATION TABLE

```
HOSPITAL 1
PATIENT MONITORING DEVICES
    PMD1
        Type
        Model No.
        Device S/N
            Technology Board Rev no.
                Signal Processing Module Version No.
            Instrument Board Rev. No
                User Interface Module Version no.
        Instrument Configuration Table
            Parameter 1
        Local Configuration Table
            Location w/i Facility
            Adult/Pediatric
        License
            License No.
                Duration
                    Start Date
                    Stop Date
                Location
        Assigned Sensors
            Sensor1
                Type
                Model No.
                Sensor S/N SENSORS
    SEN1
        Type
        Model No.
        Sensor S/N
        License
            License No.
                Duration
                    Start Date
                    Stop Date
                Location
        Associated PMD S/N
```

FIG. 5

DATABASE FIELDS FOR MASTER CONFIGURATION TABLE

```
HOSPITAL 1
    Hospital Identifier 1
    PATIENT MONITORING DEVICES
        PMD1
          ⋮
        PMDn SENSORS
        SEN1
          ⋮
        SENn
  ⋮
HOSPITALn
    Hospital Identifier n
    PATIENT MONITORING DEVICES
        PMD1
          ⋮
        PMDn SENSORS
        SEN1
          ⋮
        SENn
```

*FIG. 11*

MEDICAL MONITORING HUB

RELATED APPLICATIONS

The present disclosure is related to U.S. Provisional Application No. 62/463,461, titled "MANAGING DYNAMIC LICENSES FOR PHYSIOLOGICAL PARAMETERS IN A PATIENT MONITORING ENVIRONMENT", filed on Feb. 24, 2017 and to U.S. Provisional Application No. 62/560,008, titled "MANAGING DYNAMIC LICENSES FOR PHYSIOLOGICAL PARAMETERS IN A PATIENT MONITORING ENVIRONMENT", filed on Sep. 18, 2017, the entireties of which are incorporated herein by reference. The present disclosure is related to U.S. Provisional Application No. 62/463,490, titled "MEDICAL MONITORING HUB", filed Feb. 24, 2017, and U.S. application Ser. No. 15/905,332, titled "MEDICAL MONITORING HUB", filed on Feb. 26, 2018, now U.S. Pat. No. 10,388,120, the entireties of which are incorporated herein by reference. U.S. Pat. No. 9,436,645, titled "MEDICAL MONITORING HUB", describes various example embodiments and features related to apparatuses, systems, and methods of patient monitoring and specifically relating to a patient monitoring device and medical data communication hub, the entirety of which is incorporated herein by reference.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

The present disclosure relates to a digital database processor with database schema for dynamically managing configurations of patient monitoring devices in a patient monitoring environment.

Hospitals, nursing homes, and other patient care facilities typically include patient monitoring devices that are assigned to a patient. Patient monitoring devices generally include sensors, processing equipment, software, and displays for obtaining and analyzing the patient's physiological parameters. Medical personnel use the patient's physiological parameters to monitor a patient during various clinical situations to determine whether to change the level of medical care given to the patient. The patient monitoring devices travel with the patient as the patient moves throughout the facility.

Patient monitoring devices are configurable to meet a variety of patient needs and caregiver or care requirements. For example, a patient monitoring device can be configured for a particular area of the facility as well as for monitoring and analyzing one or more of a variety of physiological parameters. Software upgrades may be available to provide enhanced analytics. In addition, patient information entry often occurs at each device.

Further, various manufacturers produce multi-monitor devices or devices that modularly expand to increase the variety of monitoring or treatment endeavors a particular system can accomplish. However, as medical device technology expands, such multi-monitor devices begin to be obsolete the moment they are installed.

SUMMARY

According to some aspects, in a caregiver environment, a patient monitoring device comprises at least one port configured to receive a signal from a physiological sensor that senses light after it has passed through the tissue of the patient, where the signal is indicative of at least one physiological parameter of the patient in response to the sensed light associated with the patient; one or more hardware processors in communication with the at least one port, where the one or more hardware processors are configured to determine one or more measurements of the at least one physiological parameter of the patient from the received signal; and memory comprising at least a data module, a first image module, and a second image module. The data module is configured to store the one or more measurements of the at least one physiological parameter. Each of the first and second image modules comprise a system image that includes executable instructions to at least determine the one or more measurements of the at least one physiological parameter of the patient from the received signal, and one of the first and second image modules is a tested image module that includes a latest used or tested system image. The one or more hardware processors are in communication with the memory and further configured to download an image upgrade to the other of the first and second image modules that does not include the latest used or tested system image to provide an upgraded image module; boot from the upgraded image module; determine whether the one or more hardware processors are operating successfully after booting from the upgraded image module; and boot from the tested image module when the one or more hardware processors are not operating successfully after booting from the upgraded image module; where the signal is indicative of a monitoring event and where the one or more hardware processors boot from the upgraded image module, determine whether the one or more hardware processors are operating successfully, and boot from the tested image module during a time of non-monitoring.

In an embodiment, the one or more hardware processors are further configured to determine whether the image upgrade is available. In another embodiment, the one or more hardware processors are further configured determine whether the image upgrade is available based at least in part on system image identifiers of the system images residing on the first and second image modules. In a further embodiment, wherein the system identifiers comprise one of a time stamp and a version number. In an embodiment, the one or more hardware processors are further configured to download the upgraded image from the Internet.

In an embodiment, the one or more hardware processors are further configured to perform a self-check to determine whether the one or more hardware processors are operating successfully. In another embodiment, the patient monitoring device further comprises a supervisor processor, and the one or more hardware processors do not including the supervisor processor. In a further embodiment, the supervisor processor is configured to determine whether the one or more hardware processors are operating successfully by monitoring functionality of the one or more hardware processors.

In an embodiment, the one or more hardware processors are further configured to repair the upgraded image module when the one or more hardware processors are not operating successfully. In another embodiment, the one or more hardware processors are further configured to determine whether a next image upgrade is available when the one or more hardware processors are operating successfully.

According to some aspects, a method to upgrade operation of a patient monitoring device that is used in a caregiver environment is disclosed. The patient monitoring device is configured to communicate with a physiological sensor that senses light after it has passed through the tissue of a patient and generates a signal indicative of at least one physiological parameter of the patient in response to the sensed light associated with the patient. The patient monitoring device is further configured to receive the signal and determine one or more measurements of the at least one physiological parameter of the patient from the received signal. The method comprises storing in memory comprising a data module the one or more measurements of the at least one physiological parameter, where the memory further comprises at least a first image module and a second image module. The first and second image modules include system images and are configured with instructions executable by one or more hardware processors to at least determine the one or more measurements of the at least one physiological parameter of the patient from the received signal. The method further comprises downloading an image upgrade to one of the first and second image modules that is not a latest used or tested image module to provide an upgraded image module; booting from the upgraded image module; determining whether the one or more hardware processors are operating successfully after booting from the upgraded image module; and booting from the other of the first and second image modules when the one or more hardware processors are not operating successfully after booting from the upgraded image module.

In an embodiment, the method further comprises determining whether the image upgrade is available. In another embodiment, determining whether the image upgrade is available is based at least in part on system image identifiers of the system images residing on the first and second image modules. In a further embodiment, the system identifiers comprise one or more of a time stamp and a version number.

In an embodiment, the method further comprises downloading the upgraded image from the Internet. In another embodiment, the method further comprises performing a self-check to determine whether the one or more hardware processors are operating successfully. In a further embodiment, the method further comprises determining with a supervisor processor whether the one or more hardware processors are operating successfully by monitoring functionality of the one or more hardware processors.

In an embodiment, the one or more hardware processors do not include the supervisor processor. In another embodiment, the method further comprises repairing the upgraded image module when the one or more hardware processors are not operating successfully. In a further embodiment, the method further comprises determining whether a next image upgrade is available when the one or more hardware processors are operating successfully.

In order to effectively and efficiently utilize the patient monitoring devices, facility administrators need to be aware of their location and configuration in order to timely reconfigure the devices. Thus, while the flexibility of the patient monitoring devices has increased, the ability of facility administrators to timely control their usage remains challenging.

One aspect of the present disclosure comprises a dynamic licensing system that permits facility administrators to quickly enable a patient monitoring device to monitor a previously unmonitored physiological parameter. In some embodiments, the patient monitoring device has the capability to monitor a plurality of physiological parameters, but only specific physiological parameters, as defined in a configuration table residing in the device, are enabled. In other embodiments, the patient monitoring device may monitor a given set of parameters, and from time to time need to be upgraded to more recent software implementations. For those monitors where the configuration table defines a set of enabled parameters, a caregiver or administrator, even during the course of patient treatment, may determine that a new physiological parameter should be monitored. The speed at which the new physiological parameter can be enabled may be critical to patient care. To affect the change, the hospital administrator accesses a dynamic licensing module through an administrator's terminal in communication with one or more networks operably communicating with the one or more patient monitoring devices. In an embodiment, the communication may include wired, wireless, or combination communication over a hospital communication backbone, the Internet, other private or public networks or through a direct link wired or wireless communication protocol. An artisan will recognize from the disclosure herein a wide variety of commercially available mechanisms to allow a geographically local or remote administrator's terminal to communicate with a group of patient monitoring devices.

In an embodiment, the administrator selects the patient monitoring device assigned to the patient and instructs the dynamic licensing system to enable monitoring of the new physiological parameter. In an embodiment, the administrator defines how long the patient monitoring device is to be monitoring the new parameter. In another embodiment, the administrator defines the location in the hospital where the patient monitoring device is to monitor the new parameter. In an embodiment, the dynamic licensing system creates a licensing agreement to monitor the new parameter for the monitoring duration and/or in the monitoring location.

One aspect of the present disclosure is directed to an inventory control system that permits facility administrators to auto-order patient monitoring devices and sensors when the inventory becomes depleted. The administrator accesses an inventory control module through the administrator's terminal. The administrator sets the minimum inventory criteria for each model of the patient monitoring devices and sensors kept in the hospital's inventory. In an embodiment, the inventory control system updates the quantity of stock when patient monitoring devices and sensors are assigned to a patient. The inventory control system compares the number of devices and sensors in stock with the minimum quantity to keep in stock, as defined by the administrator. Further, the inventory control system automatically orders additional patient monitoring devices and sensors when the stock quantities fall below the minimum specified quantity. The inventory control system also updates the inventory data when new devices and sensors are placed in the inventory. In other embodiments, the inventory control system determines orders should be placed for a monitoring device or a device accessory, including, for example, cables, connectors, sensors, securing tapes or attachment mechanisms, memory devices, or the like, and when such determination is made, the system sends a message to the administrator alerting him or her to the need for the order or requesting authorization from the administrator for the order. In still other embodiments, the inventory control system communicates the need for an order into a workflow system used by a facility or group of facilities, the workflow system often seeking one or more authorizations to create, manage and/or fill the order.

Another aspect of the present disclosure includes an automatic software version control system. In an embodiment, the patient monitoring devices comprise technology boards that utilize signal processing software to monitor the patient's physiological parameters. The patient monitoring devices further comprise instrument boards that utilize interface software to display the monitored physiological parameters and run the user interface.

Software programs are constantly being enhanced to provide additional capabilities. One way to update the patient monitoring devices with a new version of software appropriate for a specific model and version of a specific board is to manually upload the new version from a data storage device, such as a flash drive. However, this method can be prone to errors. An incorrect version or an incompatible version of the software can be inadvertently uploaded. For example, a certain technology board may include hardware capable of determining only a subset of parameters. Were an update to occur with software designed for parameters beyond the board's capabilities, such upgraded software could cause unwanted failures or oddities in performance. Further, it is time consuming and labor intensive to individually update the patient monitoring devices.

In an embodiment, the administrator accesses a software version control module through the administrator's terminal and the administrator instructs the software version control system to upgrade, in some embodiments, automatically upgrade, the patient monitoring devices in the hospital's active inventory. In an embodiment, the active inventory comprises the patient monitoring devices in communication with the hospital's communication backbone and/or other network. The software version control system determines whether the patient monitoring device is currently monitoring a patient's physiological parameters. In one embodiment, if the device is busy monitoring physiological parameters, the software version control system waits until the device is available to ensure that patient safety is not compromised.

When the patient monitoring device is available, the software version control system automatically verifies versions of the signal processing module and the user interface module residing on the patient monitoring device and pushes over any more recent compatible software images, for example, an image of the latest compatible software version for each module. In an embodiment, the software image is pushed via the hospital's communication backbone. In another embodiment, the software image is pushed via the Internet. In other embodiments, the administrator may advantageously monitor alerts that inform him or her which devices have more recent versions of software available from the device manufacturer. When such a more recent version is available, the administrator may select to have an image pushed to that device.

in another embodiment, administrators have an override option. The software version control system checks whether the override option is selected, and if the patient monitoring device is monitoring a patient's physiological parameters and the override option is selected, the software version control system pushes an image of the software upload onto the patient monitoring device.

After the software upload is complete, and at an appropriate time, such as a time of non-monitoring, the software version control system resets the patient monitoring device. In an embodiment, the software version control system cycles power on the patient monitoring device. The software version control system further updates the hospital inventory database with the updated software versions, as well as updating the configuration table residing in the patient monitoring device with the revised software versions.

According to some aspects, a patient monitoring device can include a processor having a memory module including a plurality of memory partitions. The plurality of memory partitions can include a data module, and first image module and a second image module. When a system image upgrade is available, the first module or the second module can be upgraded to include the system image upgrade.

According to some aspects, a processor of a patient monitoring device is capable of booting from the first image module or the second image module. The processor determines which of the image modules include the latest system image and attempts to boot from the image module determined to include the latest system image. If the fails to boot from the image module determined to include the latest system image, the processor boots from the other image module. The processor determines whether an image upgrade is available. Responsive to a determination that an image upgrade is available, the processor upgrades the image module which was not used to successfully boot or did not allow the processor to function correctly.

According to some aspects, a patient monitoring device includes a first processor and a second processor which are separate and distinct from each other. The first processor is configured to query the second processor and receive data associated and/or correlated with one or more operating conditions of the second processor. The first processor is further configured to determine a health status of the second processor based at least in part on the data associated and/or correlated with the one or more operating conditions of the second processor. Based at least in part on a determination that the health status of the second processor does not satisfy a first threshold health status, the first processor is configured to initiate maintenance on the second processor. The second processor is configured to query the first processor and receive data associated and/or correlated with one or more operating conditions of the first processor. The second processor is further configured to determine a health status of the first processor based at least in part on the data associated and/or correlated with the one or more operating conditions of the first processor. Based at least in part on a determination that the health status of the first processor does not satisfy a first threshold health status, the second processor is configured to initiate maintenance on the first processor.

The patient monitoring device of the preceding paragraph may also include a first processor and second processor having different capabilities. The first processor has higher capabilities than the second processor.

According to some aspects, a patient monitoring device can include a processor having a motherboard and a daughterboard. The motherboard can include a main processor. The daughterboard is configured connect to the motherboard and configured to receive an accessory upgrade. Upon receipt of an accessory upgrade by the daughterboard, the patient monitoring device can receive a safety certification after the daughterboard is certified.

According to some aspects, a patient monitoring device can include a battery which maintains a longer life because it is not fully charged. The patient monitoring device is configured to enter a shipping mode. The shipping mode disconnects the battery from the patient monitor, thereby ensuring that the battery is not discharged into patient monitor electronics.

According to some aspects, a patient monitoring device includes a first processor and a second processor. The first processor is configured to monitor at least one of health status, one or more vital signs, or one or more physiological parameters of a patient. The second processor is configured to determine a recommended care protocol based at least in part on the monitored health status, one or more vital signs, or one or more physiological parameters of the patient. The second processor is further configured to provide an indication of the determined recommended care protocol at an end user point.

According to some aspects, a system includes a first server and a second server. The first server is configured to generate one or more system image upgrades. Each of the one or more system image upgrades is useful for only one specific device having a specific hardware encryption configuration. The first server is further configured to break the one or more system image upgrades into a plurality of data packets for transmission and transmit one or more of the plurality of data packets to the second server. The second server is configured to receive the one or more data packets and reassemble the data packets into the one or more system image upgrades. The second server is further configured to upload a system image upgrade to the specific device having the specific hardware encryption configuration.

According to some aspects, system that executes database schema to manage dynamic licenses for physiological parameters in a patient monitoring environment is disclosed. The system comprises a first patient monitoring system comprising a first physiological sensor configured to sense light after it has passed through tissue of a first patient and generate a first signal indicative of one or more first physiological parameters of the first patient in response to the sensed light associated with the first patient, and a first patient monitoring device in communication with the first physiological sensor and configured to receive the first signal and determine one or more measurements of the one or more first physiological parameters of the first patient from the received first signal; a second patient monitoring system comprising a second physiological sensor configured to sense light after it has passed through tissue of a second patient and generate a second signal indicative of one or more second physiological parameters of the second patient in response to the sensed light associated with the second patient, and a second patient monitoring device in communication with the second physiological sensor and configured to receive the second signal and determine one or more measurements of the one or more physiological parameters of the second patient from the received second signal; and a service appliance comprising an administrator terminal, memory storing a configuration table, and one or more hardware processors, the service appliance in communication with the first and second patient monitoring devices over at least one of a wired communication backbone and a wireless network, the one or more hardware processors configured to: receive licensing information for the first patient monitoring device, wherein the licensing information comprises an indication of at least a licensed physiological parameter, an indication of one or more unlicensed physiological parameters that the first patient monitoring device is disabled from monitoring, and a licensing duration; retrieve device information associated and/or correlated with the first patient monitoring device from the configuration table, the device information comprising an address of the first patient monitoring device; transmit a message addressed to the first patient monitoring device, the message comprising instructions to enable at least one of the one or more unlicensed physiological parameters to permit the first patient monitoring device to monitor the at least one enabled physiological parameter; and generate a license to indicate that the first patient monitoring device is configured to monitor the at least one enabled physiological parameter for the licensing duration, the license comprising a license number; and update the device information of the first patient monitoring device in the configuration table with an indication of the at least one enabled physiological parameter and the license number.

In an embodiment, the at least a licensed physiological parameter comprises at least one of oxygen saturation (SpO2), hemoglobin (Hb), oxyhemoglobin (HbO2), total hemoglobin, carboxyhemoglobin, methemoglobin, perfusion index (Pi), and pulse rate (PR). In another embodiment, the one or more unlicensed physiological parameters comprise at least one of blood pressure, temperature, electrocardiogram (ECG), motion data, accelerometer data, respiration, continuous blood pressure, pleth variability index, oxygen content, oxygen reserve index, acoustic respiration rate (RRa), and respiration rate from the pleth.

In an embodiment, 4 the licensing information further comprises a location in the patient monitoring environment where the first patient monitoring device is permitted to monitor the at least one enabled physiological parameter and the one or more hardware processors are further configured to update the device information of the first patient monitoring device in the configuration table with the location. In another embodiment, the one or more hardware processors are further configured to adjust, in response to the licensing information, a quantity of available licenses for the at least one enabled physiological parameter in an inventory database. In another embodiment, the one or more hardware processors are further configured to automatically order additional licenses for the at least one enabled physiological parameter when the quantity of available licenses for the at least one enabled physiological parameter in the inventory database falls below a minimum quantity.

In an embodiment, the first patient monitoring device includes a device processor and device memory including a first image module and a second image module, the first patient monitoring device configured to determine which of the first image module and the second image module is the latest image module. In another embodiment, the first patient monitoring device is further configured to boot the device processor from the latest image module of the first and second image modules and boot the device processor from the other of the first and second image modules when the latest image module causes the first patient monitoring device to operate incorrectly. In another embodiment, the one or more hardware processors further configured to access a software upgrade database to determine whether an image upgrade is available for the first patient monitoring device, and upgrade one of the first and second image modules with the available image upgrade.

According to some aspects, a method to manage dynamic licenses for physiological parameters in a patient monitoring environment that includes one or more patient monitoring devices, each patient monitoring device in communication with at least one of a communication backbone and the Internet, each patient monitoring device being addressable is disclosed. The method comprises, as implemented by one or more computing devices configured with specific executable instructions, receiving licensing information for a patient monitoring device, wherein the licensing information comprises an indication of a physiological parameter that the patient monitoring device is disabled from monitoring and a licensing duration; retrieving device information associated and/or correlated with the patient monitoring device from a configuration table, the device information comprising an address of the patient monitoring device; transmitting a message addressed to the patient monitoring device, the message comprising instructions to enable the physiological parameter to permit the patient monitoring device to calculate values for the physiological parameter; generating a license to indicate that the patient monitoring device is configured to monitor the physiological parameter for the licensing duration, the license comprising a license number; and updating the device information in the configuration table for the patient monitoring device with an indication of the enabled parameter and the license number.

In an embodiment, the method further comprises updating a quantity of available patient monitoring devices in an inventory database in response to the licensing information, and automatically ordering additional patient monitoring devices when a quantity of available patient monitoring devices in the inventory database falls below a minimum quantity. In another embodiment, the method further comprises receiving software upgrade instructions for the patient monitoring device, pushing an upgraded version of modules residing on the patient monitoring device to memory on the patient monitoring device, and determining that an override is enabled, and after determining that the override is enabled, downloading the upgraded version of the modules into the patient monitoring device.

According to some aspects, a digital processing system that executes database schema to manage dynamic licenses for physiological parameters in a patient monitoring environment is disclosed. The system comprises at least one patient monitoring device; and a server in a first computing device comprising computer hardware configured to: receive licensing information for the at least one patient monitoring device, wherein the licensing information comprises an indication of a physiological parameter that the at least one patient monitoring device is disabled from monitoring and a licensing duration; retrieve device information associated and/or correlated with the at least one patient monitoring device from a configuration table, the device information comprising an address of the at least one patient monitoring device; transmit a message addressed to the at least one patient monitoring device, the message comprising instructions to enable the physiological parameter to permit the at least one patient monitoring device to calculate values for the physiological parameter; generate a license to indicate that the at least one patient monitoring device is configured to monitor the physiological parameter for the licensing duration, the license comprising a license number; and update the device information in the configuration table for the at least one patient monitoring device with an indication of the enabled parameter and the license number.

In an embodiment, the computer hardware is further configured to adjust an inventory database that comprises quantities of available patient monitoring devices and available licenses in response to the licensing information and the computer hardware is further configured to automatically generate a purchase order for additional patient monitoring devices when the adjusted quantity available patient monitoring devices is less than a minimum quantity. In another embodiment, the computer hardware is further configured to automatically verify versions of modules residing on the at least one patient monitoring device and update the device information of the at least one patient monitoring device in the configuration table with the verified versions of the modules residing on the at least one patient monitoring device, automatically push updated images of the modules to the at least one patient monitoring device, and automatically reset the at least one patient monitoring device after pushing the updated images of the modules when the at least one patient monitoring device is at a time of non-monitoring and update the configuration table with a version of the updated images of the modules residing on the at least one patient monitoring device.

According to some aspects, a digital processing system that executes database schema to manage inventory for patient monitoring devices that monitor physiological parameters in a patient monitoring environment and for licenses to monitor the physiological parameters associated and/or correlated with the patient monitoring devices is disclosed. The system comprises at least one patient monitoring device; and a server in a first computing device comprising computer hardware configured to: receive licensing information for the at least one patient monitoring device, wherein the licensing information comprises an indication of at least one physiological parameter that the at least one patient monitoring device is licensed to monitor and a licensing duration; adjust in an inventory control database a quantity of licenses associated and/or correlated with the at least one physiological parameter based at least in part on the licensing information; receive auto-order criteria; and automatically generate a purchase order to order licenses associated and/or correlated with the at least one physiological parameter based at least in part on the auto-order criteria and the adjusted inventory control database.

In an embodiment, the computer hardware is further configured to adjust in the inventory control database a quantity of patient monitoring devices and the quantity of licenses associated and/or correlated with the at least one physiological parameter at an expiration of the licensing duration, to automatically generate a purchase order to order patient monitoring devices when the adjusted quantity of patent monitoring devices falls below a minimum quantity of patient monitoring devices, to receive software upgrade instructions for the at least one patient monitoring device and push an upgraded image module to the at least one patient monitoring device in response to the software upgrade instructions, and to update a configuration table with a version of the upgraded image model.

According to some aspects, a digital processing system that executes database schema to manage software upgrades for patient monitoring devices that monitor physiological parameters in a patient monitoring environment is disclosed. The system comprises at least one patient monitoring device; and a server in a first computing device comprising computer hardware configured to: receive software upgrade instructions for the at least one patient monitoring device; retrieve device information associated and/or correlated with the at least one patient monitoring device from a configuration table, the device information comprising an address of the at least one patient monitoring device; and push, using the address, an upgraded image module to the at least one patient monitoring device for storage in memory within the at least one patient monitoring device.

In an embodiment, the computer hardware is further configured to determine whether the at least one patient monitoring device is actively monitoring, determine whether an override is enabled, download the upgraded image module in the at least one patient monitoring device during active monitoring when the override is enabled, and download the upgraded image module in the at least one patient monitoring device at a period of non-monitoring when the override is disabled. In another embodiment, the computer hardware is further configured to update the device information for the at least one patient monitoring device in the configuration table with a version of the upgraded image module.

In an embodiment, the computer hardware is further configured to reset the at least one patient monitoring device to cause a processor in the at least one patient monitoring device to reboot using the upgraded image module. In another embodiment, memory in the at least one patient monitoring device is configured to store the upgraded image module and a previous version of an image module, and the at least one patient monitoring devise is configured to reboot the processor using the previous version of the image module when the reboot of the processor using the upgraded image module causes the at least one patient monitoring device to operate incorrectly.

According to some aspects, a patient monitoring system is disclosed. The patient monitoring system comprises a physiological sensor configured to sense light after it has passed through tissue of a patient and generate a signal indicative of one or more physiological parameters of the patient in response to the sensed light associated with the patient; and a patient monitoring device in communication with the physiological sensor and configured to receive the signal and determine one or more measurements of the one or more physiological parameters of the patient from the received signal. The patient monitoring device comprises a processor including a processing circuit and memory including a first image module and a second image module, where the processing circuit is configured to determine which of the first image module and the second image module includes a latest system image; boot the processor with the one of the first and second image module that includes the latest system image; and reboot the processor with the other of the first and second image module when a failure occurs due to booting the processor with the latest system image.

In an embodiment, the processing circuit is further configured to upgrade one of the first and second image modules in response to availability of an upgraded image module, to upgrade the other of the first and second image modules with the upgraded image when the boot of the processor with the latest system image is successful, and to upgrade the one of the first and second image module that includes the latest system image when boot of the processor with the latest system image is unsuccessful.

Aspects disclosed herein advantageously provide software-based non-abstract improvements for physiological parameter monitoring of patients in a patient monitoring environment. Embodiments disclosed herein advantageously provide a new type of physiological parameter license that allows an administrator or other patient care personnel, through the service appliance, to tailor physiological parameter licenses for specific patients in real time or near real time when monitoring is critical to the patients' health. Embodiments disclosed herein advantageously provide a new type of physiological parameter monitoring inventory that automatically generates purchase orders, through the service appliance, for physiological parameter monitoring devices in real time or near real time when maintaining physiological parameter monitoring inventory is critical to the patients' health. Embodiments disclosed herein advantageously provide a new type of software upgrade process that allows an administrator or other patient care personnel, through the service appliance, to upgrade physiological parameter monitoring software for specific patients or throughout the patient monitoring environment in real time or near real time when monitoring is critical to the patients' health.

Aspects disclosed herein advantageously solve specific problems in computer system monitoring of physiological parameters for patients in a patient monitoring environment. Embodiments disclosed herein advantageously provide specific solutions to create in real time or near real time physiological parameter licenses in a patient monitoring environment where timeliness of physiological parameter monitoring may be critical to patient health. Embodiments disclosed herein advantageously provide specific solutions to automatically generate purchase orders or update patient monitoring inventory in a patient monitoring environment where availability of patient monitoring inventory may be critical to patient health. Embodiments disclosed herein advantageously provide specific solutions to provide in real time or near real time software upgrades to patient monitoring device that monitor physiological parameters in a patient monitoring environment where enhancing or correcting physiological parameter monitoring may be critical to patient health.

Aspects disclosed herein comprise an ordered combination that is not conventional to advantageously provide real time or near real time generation of physiological parameter licenses for patient care in a patient monitoring environment. Embodiments disclosed herein advantageously provide physiological parameter licensing information that is converted into physiological parameter monitoring instructions for patient monitoring devices that are deployed at multiple locations within a patient monitoring network. Embodiments disclosed herein advantageously provide physiological parameter software upgrade information that is converted into software upgrade instructions for patient monitoring devices that are deployed at multiple locations within a patient monitoring network. Embodiments disclosed herein advantageously provide inventory information that is converted into purchase orders for patient monitoring devices that are deployed at multiple locations within a patient monitoring network.

Aspects disclosed herein advantageously provide a distributed architecture for monitoring of physiological parameters in a patient monitoring environment. Embodiments disclosed herein describe a system comprising a hospital communication backbone that provides communication paths between distributed patient monitoring devices of the system and a service appliance of the system. Advantageously, the system correlates physiological parameter licensing information and/or inventory information and/or software upgrade information with a configuration table for each patient monitoring device of the distributed system. The configuration table comprising the correlated information advantageously provides a central point to quickly enable physiological parameter monitoring, order physiological parameter monitoring inventory, and/or upgrade physiological monitoring software that may be critical to patient care.

For purposes of summarizing the disclosure, certain aspects, advantages and novel features are discussed herein. It is to be understood that not necessarily all such aspects, advantages or features will be embodied in any particular embodiment of the invention, and an artisan would recognize from the disclosure herein a myriad of combinations of such aspects, advantages or features.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

FIG. 5 is an exemplary database structure used to dynamically manage patient monitoring devices and sensors in a patient monitoring environment, according to certain embodiments.

FIG. 11 is an exemplary database structure used to dynamically manage patient monitoring devices and sensors in multiple patient monitoring environments, according to certain embodiments.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

Figure 1:
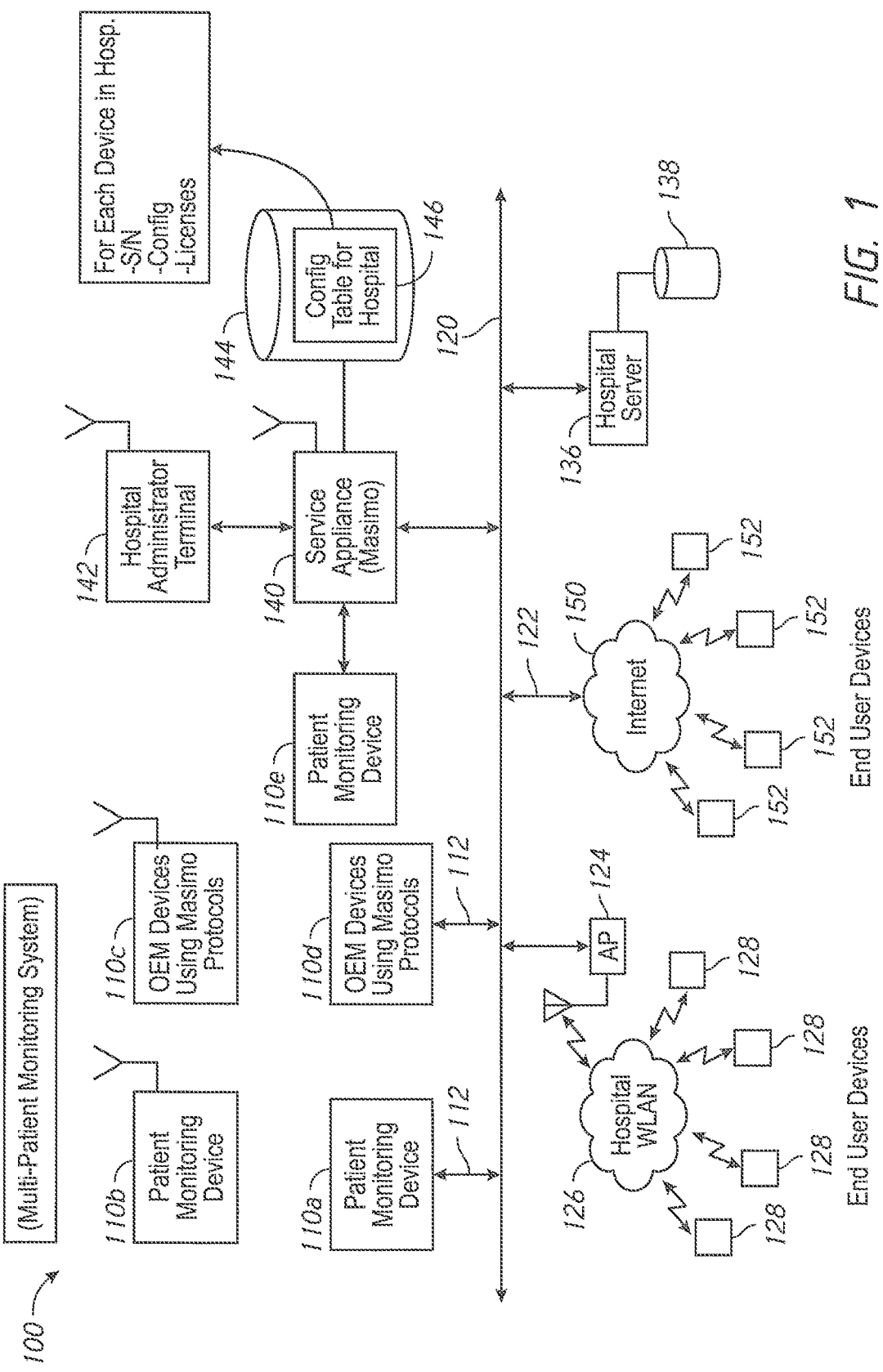
FIG. 1 is an exemplary block diagram showing a system to dynamically control a patient monitoring environment, according to certain embodiments.

FIG. 1 illustrates an embodiment of a system 100 to dynamically control a patient monitoring environment. The patient monitoring environment is typically found in a hospital or other patient care facility. Throughout this disclosure, the terms hospital, patient care facility, and facility are used interchangeably. The system 100 includes an open network architecture using off-the-shelf hardware and communication protocols. This architecture in various implementations is a shared, or open, network that includes a network bus 120 (e.g., an Ethernet backbone), and a hospital network 126, such as a WLAN. Data can be sent over the shared network through an access point 124 or other wireless or wired transmitter. In addition, the shared network may further include a connection 122 to the Internet 150. Other networks or combinations of networks, public or private, wired or wireless, cellular or other, are recognizable to an artisan from the disclosure herein, and could be accessed in manners familiar to an artisan to provide the communications between devices and other computing systems disclosed herein.

The system 100 further includes patient monitoring devices 110 and end user devices 128, 152. The patient monitoring devices 110 are associated and/or correlated with one or more sensors and monitor physiological parameters of patients. In certain embodiments, each patient monitoring device 110 is used by one medical patient. The patient monitoring devices 110 form a network of patient monitoring devices 110, each of which can communicate with the end user devices 128, 152 over the shared network. Sensors associated and/or correlated with the patient monitoring devices 110 measure physiological signals and the patient monitoring devices process the signals and calculate the patient's physiological parameters based at least in part on the processed signals from the sensors.

In certain embodiments, the patient monitoring devices 110a, 110d send data over the shared network through the access point 124 or other wireless or wired transmitter. Alternatively, the patient monitoring devices 110b, 110c may communicate physiological information directly to end users over the Internet 150. End users such carrying notifier devices, e.g., end user devices 128, 152 connected to the hospital WLAN 126 or the Internet 150, may receive real-time viewing of physiological patient parameters and waveforms on demand or in the event of an alarm or alert.

In some implementations, a server 136 may be included in the system 100. The server 136 in these implementations is generally a computing device such as a blade server or the like. In certain embodiments, the server 136 is an appliance server, which at times could be housed in a data closet. In some embodiments, the server 136 is a server located at a central nurses' station, such as a workstation server.

The server 136 receives data packages comprising physiological monitoring data from a plurality of patient monitoring devices 110 and stores the physiological monitoring data in a storage device 138. In certain embodiments, this storage device 138 archives long-term patient data. This patient data may be maintained even after the patient is discharged. In storing patient data, the server 136 may act as an interface between the shared network and an external electronic medical record (EMR) system. The access and storage of patient data may advantageously comply with all governmental and industry standards for patient data, including, for example, HIPPA requirements or the like.

The system 100 further comprises a service appliance 140 that includes a server, a terminal 142, and a storage device 144. The service appliance 140 is in wired or wireless communication with the network bus 120, the Internet 150, the terminal 142, and the storage device 144. In an embodiment, the patient monitoring devices 110e communicate directly with the service appliance 140.

In an embodiment, the server 136 comprises the service appliance 140. In another embodiment, the storage device 138 comprises the storage device 144.

In an embodiment, the service appliance 140 comprises a dynamic licensing control system that is configured to enable patient monitoring devices 110 to monitor previously unmonitored physiological parameters. The service appliance 140 may also advantageously include an inventory control system configured to auto-order or create requests for orders of patient monitoring devices 110 and peripheral accessories including sensors when certain ones, some, or all of the inventory becomes depleted or reaches predetermined minimal levels. Accessories may include cables, bandages, attachment mechanisms, and the like. The service appliance 140 may also include a software version control system that is configured to at least upgrade software associated and/or correlated with the patient monitoring devices 110 in the active inventory.

The storage device 144 comprises a configuration table 146 for the hospital. The hospital configuration table 146 includes information relating to the patient monitoring devices 110 and the sensors for the hospital. This information is accessed by some or all of the licensing control system, the inventory control system, and the software version control system.

In an embodiment, the terminal 142 comprises an administrator's terminal and is used by the facility administrator to manage the patient monitoring devices 110 and sensors. In an embodiment, the administrator's terminal comprises user interface hardware, such as, but not limited to a keyboard, a mouse, and a monitor, that permit the administrator to interface with at least the dynamic licensing control system, the inventory control system, and the software version control system.

Figure 2A:
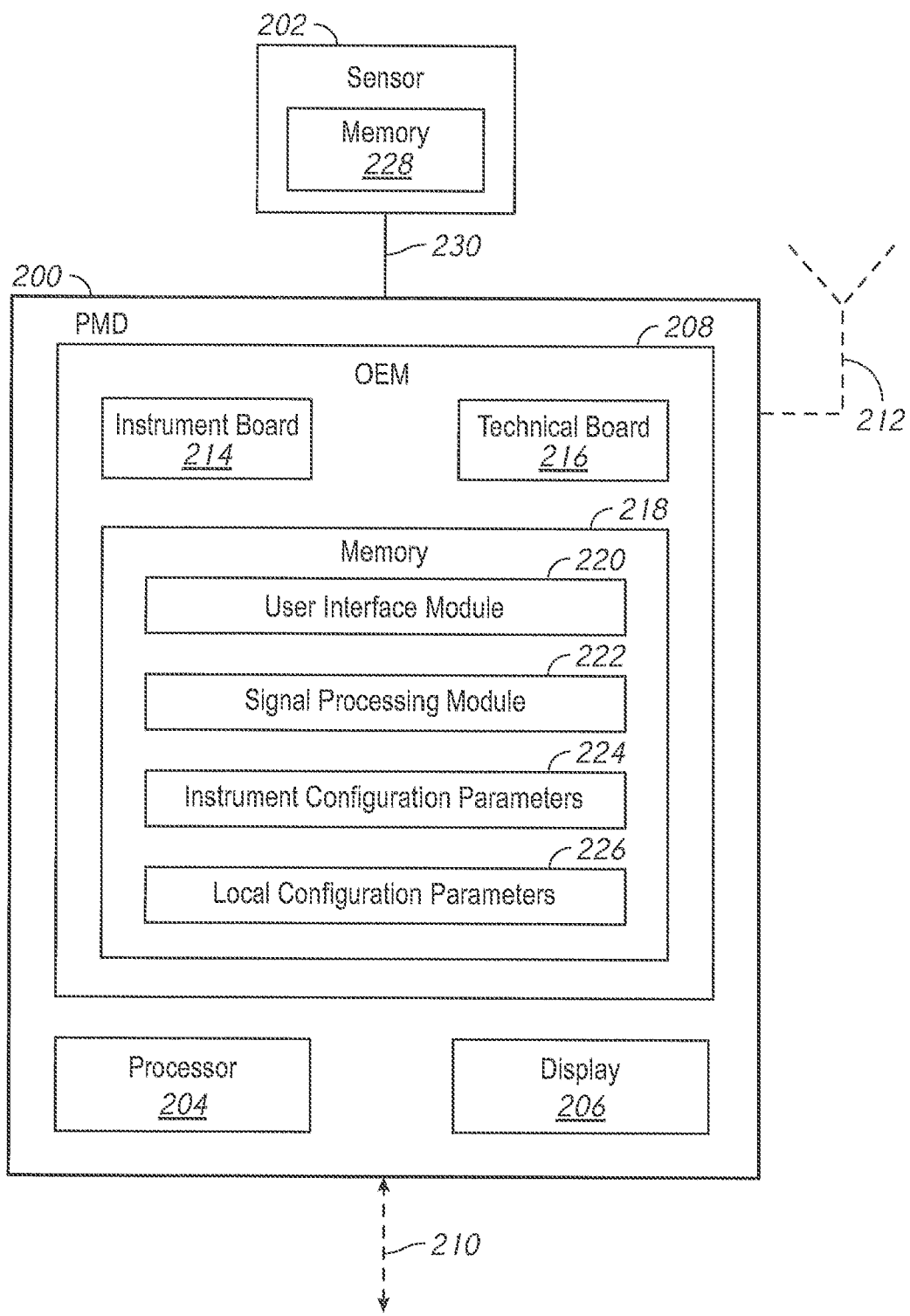
FIG. 2A is an exemplary block diagram of a patient monitoring device, according to certain embodiments.

FIG. 2A is an exemplary block diagram of a patient monitoring device. In an embodiment, the patient monitoring device comprises an exemplary docked portable patient monitor 200, which may be referred to herein as the patient monitoring device 200. The patient monitoring device 200 may advantageously comprise an oximeter, co-oximeter, respiratory monitor, depth of sedation monitor, noninvasive blood pressure monitor, vital signs monitor or the like, such as those commercially available from Masimo Corporation of Irvine, CA, and/or disclosed in U.S. Patent Publication Nos. 2002/0140675, 2010/0274099, 2011/0213273, 2012/0226117, 2010/0030040; U.S. Patent Application Ser. Nos. 61/242,792, 61/387,457, 61/645,570, 13/554,908 and U.S. Pat. Nos. 6,157,850, 6,334,065, and the like.

The patient monitoring device 200 comprises a first processor 204, a display, 206, and an OEM board 208. The patient monitoring device 200 further comprises one or more cables 210 and an antenna 212 for wired and wireless communication, respectively.

The OEM board 208 comprises an instrument board 214, a core or technical board 216, and memory 218. In an embodiment, the memory 218 comprises a user interface module 220, a signal processing module 222, instrument configuration parameters 224, and local configuration parameters 226.

The patient monitoring device 200 may communicate with a variety of noninvasive and/or minimally invasive sensors 202 such as optical sensors with light emission and detection circuitry, acoustic sensors, devices that measure blood parameters from a finger prick, cuffs, ventilators, ECG sensors, pulse oximeters, and the like.

One or more of the sensors 202 are attached to a medical patient. The sensors 202 obtain physiological information from a medical patient and transmit this information to the technical board 216 through cables 230 or through a wireless connection (not shown). In certain embodiments, the physiological information includes one or more physiological parameters or values and waveforms corresponding to the physiological parameters.

The technical board 216 receives physiological information from the sensors 202. The technical board 216 of certain embodiments includes a circuit having a second processor, which may be the same as the first processor 204, and input ports for receiving the physiological information. The technical board 216 accesses the signal processing module 222 to process the physiological information in the second processor. In addition, the technical board 216 contains one or more output ports, such as serial ports. For example, an RS232, RS423, or autobaud RS232 (serial interface standard) port or a universal serial bus (USB) port may be included in the technical board 216.

The technical board 216 and the signal processing module 222 comprise a sensor processing system for the patient monitoring device 200. In certain embodiments, the sensor processing system generates waveforms from signals received from the sensors 202. The sensor processing system may also analyze single or multiparameter trends to provide early warning alerts to clinicians prior to an alarm event. In addition, the sensor processing system in certain embodiments generates alarms in response to physiological parameters exceeding certain safe thresholds.

Example alerts include no communication with the patient monitoring device 200, alarm silenced on the patient monitoring device 200, instrument low battery (patient monitoring device 200), and transmitter low battery. Example physiological parameters include SpO2 levels, high and low SpO2, high and low PR, HbCO level, HbMET level, pulse rate, perfusion index (PI), signal quality, HbCO, HbMET, and desat index. Additional example alarms include SpO2 alarms, high and low SpO2 alarms, high and low PR, HbCO alarms, HbMET alarms, pulse rate alarms, no sensor alarms, sensor off patient alarms, sensor error, low perfusion index alarm, low signal quality alarm, HbCO alarm, HbMET alarm, PI trend alarm, and desat index alarm.

The instrument board 214 receives the waveforms, alerts, alarms, and the like from the technical board 216. The instrument board 214 of certain embodiments includes a circuit having a third processor, which may be the same as the first processor 204, and input ports for receiving the waveforms, alerts, and alarms from the technical board 216 and output ports for interfacing with the display 206, a speaker or other device capable of producing an audible indication. The instrument board 214 accesses the user interface module 220 to process the waveforms, alerts, and alarms to provide indications of the waveforms, alerts, alarms or other data associated and/or correlated with the physiological parameters monitored by the sensors 202. In an embodiment, the indications are displayed on the display 206. In other embodiments, the alerts and alarms are audible. In other embodiments, the indications, alerts, and alarms are communicated to the end user devices 128, 152 through the hospital backbone 120, the hospital WLAN 126, and/or the Internet 150.

Additionally, the instrument board 214 and/or the technical board 216 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 214 and/or the technical board 216 may comprise a large number of electronic components organized in a large number of ways.

Because of the versatility needed to process many different physiological parameters, the technical board 216 further comprises a revision number or other indication of the circuit design and capabilities of a specific technical board 216.

Likewise, because of the versatility needed to display the processed physiological parameters for use by many different end users, the instrument board 214 further comprises a revision number or other indication of the circuit design and capabilities of the specific instrument board.

Software is also subject to upgrading to increase its capabilities. The signal processing module 222 further comprises a version number or other indication of the code found in the specific signal processing module 222. Likewise, the user interface module 220 further comprises a version number or other indication of the code found on the specific user interface module 220.

In an embodiment, some or all of the serial numbers, the model numbers, and the revision numbers of the technical board 216 and the instrument board 214 that comprise the specific patient monitoring device 200 are stored in the instrument configuration parameters 224. Further, the version numbers of the signal processing module 222 and the user interface module 220 are stored in the instrument configuration parameters 224. In an embodiment, the instrument configuration parameters 224 further comprise indications of the physiological parameters that are enabled, and indications of the physiological parameters that are capable of being enabled for the patient monitoring device 200.

In some embodiments, the location of the patient monitoring device 200 affects the sensitivity at which a physiological parameter is monitored. For example, a physiological parameter may be monitored with greater sensitivity when the patent monitoring device 200 is located in the neonatal intensive care unit (NICU), OR or surgical ICU than when it is located in an adult patient's room. In an embodiment, the location of the patient monitoring device 200 may affect the availability of the device for another patient. For example, a patient monitoring device 200 located in the hospital discharge area may be available for another patient, whereas one located in a patient's room may not be available anytime soon.

In an embodiment, the local configuration parameters 226 comprise a location of the patient monitoring device 200 within the facility, an indication of whether the device is configured for adult or pediatric monitoring, and the like.

In an embodiment, the sensor 202 comprises memory 228. In an embodiment, the memory 228 comprises information associated and/or correlated with the sensor 202, such as, but not limited to a sensor type, a sensor model number, a sensor revision number, a sensor serial number, and the like.

In an embodiment, the patient monitoring device 200 comprises a Radical-7® Rainbow SET Pulse Oximeter by Masimo Corporation, Irvine, CA In an embodiment, the OEM board 208 is produced by Masimo Corporation, Irvine, CA and used by others to produce patient monitoring devices 110c, 110d.

Figure 2B:
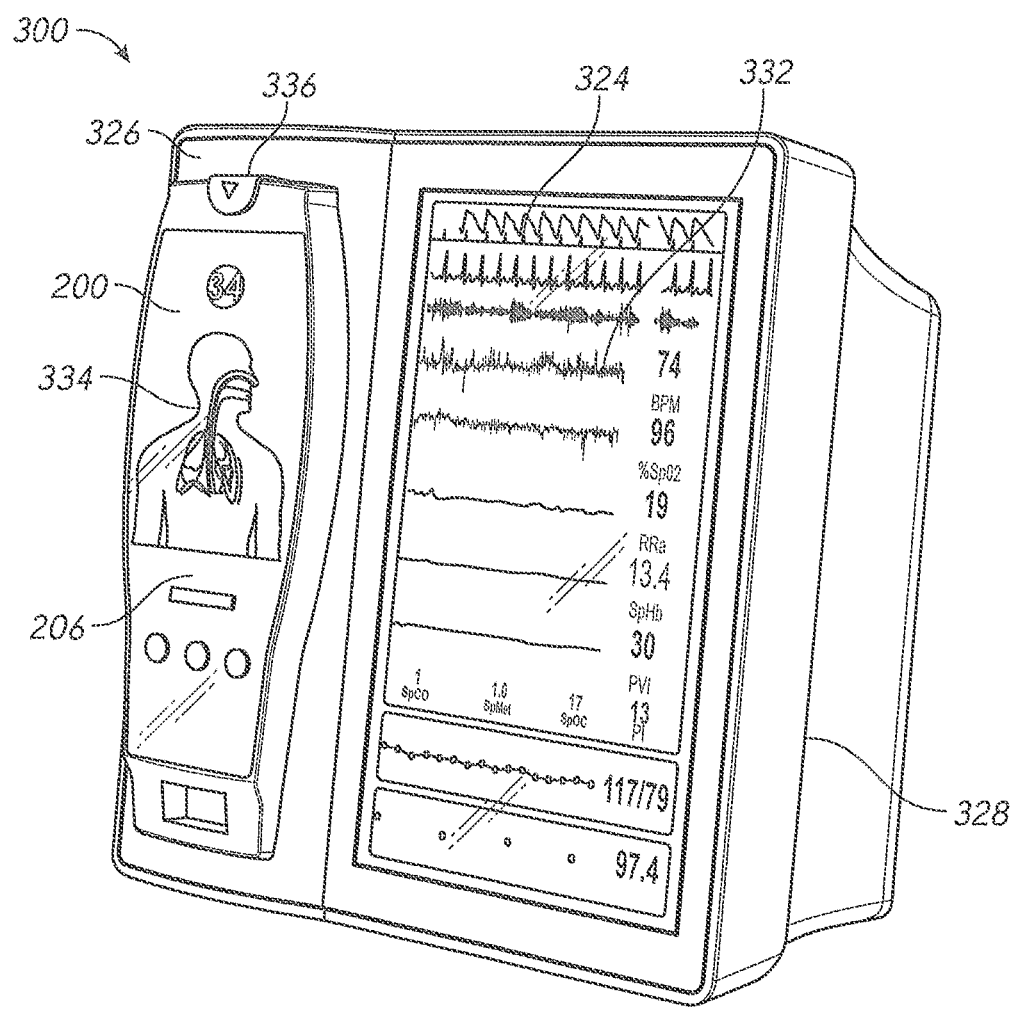
FIG. 2B is a perspective view of another patient monitoring device including a hub and the exemplary patient monitoring device of FIG. 2, according to certain embodiments.

FIG. 2B illustrates a perspective view of another exemplary patient monitoring device, such as a medical monitoring hub with the exemplary docked portable patient monitoring device 200, the combination of which may also be referred to herein as a patient monitoring device or patient monitoring system 300. The hub includes a display 324, and a docking station 326, which in an embodiment is configured to mechanically and electrically mate with the portable patient monitoring device 200, each housed in a movable, mountable and portable housing 328. The housing 328 includes a generally upright inclined shape configured to rest on a horizontal flat surface, although the housing 328 can be affixed in a wide variety of positions and mountings and comprise a wide variety of shapes and sizes.

In an embodiment, the display 324 may present a wide variety of measurement and/or treatment data in numerical, graphical, waveform, or other display indicia 332. In an embodiment, the display 324 occupies much of a front face of the housing 328; although an artisan will appreciate the display 324 may comprise a tablet or tabletop horizontal configuration, a laptop-like configuration or the like. Other embodiments may include communicating display information and data to a table computer, smartphone, television, or any display system recognizable to an artisan. The upright inclined configuration of FIG. 2B presents display information to a caregiver in an easily viewable manner. The patient monitoring device 300 may display information for a variety of physiological parameters, such as but not limited to oxygen saturation (SpO2), hemoglobin (Hb), oxyhemoglobin (HbO2), total hemoglobin, carboxyhemoglobin, methemoglobin, perfusion index (Pi), pulse rate (PR) of blood pressure, temperature, electrocardiogram (ECG), motion data, accelerometer data, respiration, continuous blood pressure, pleth variability index, oxygen content, oxygen reserve index, acoustic respiration rate (RRa), and respiration rate from the pleth.

Figure 2C:
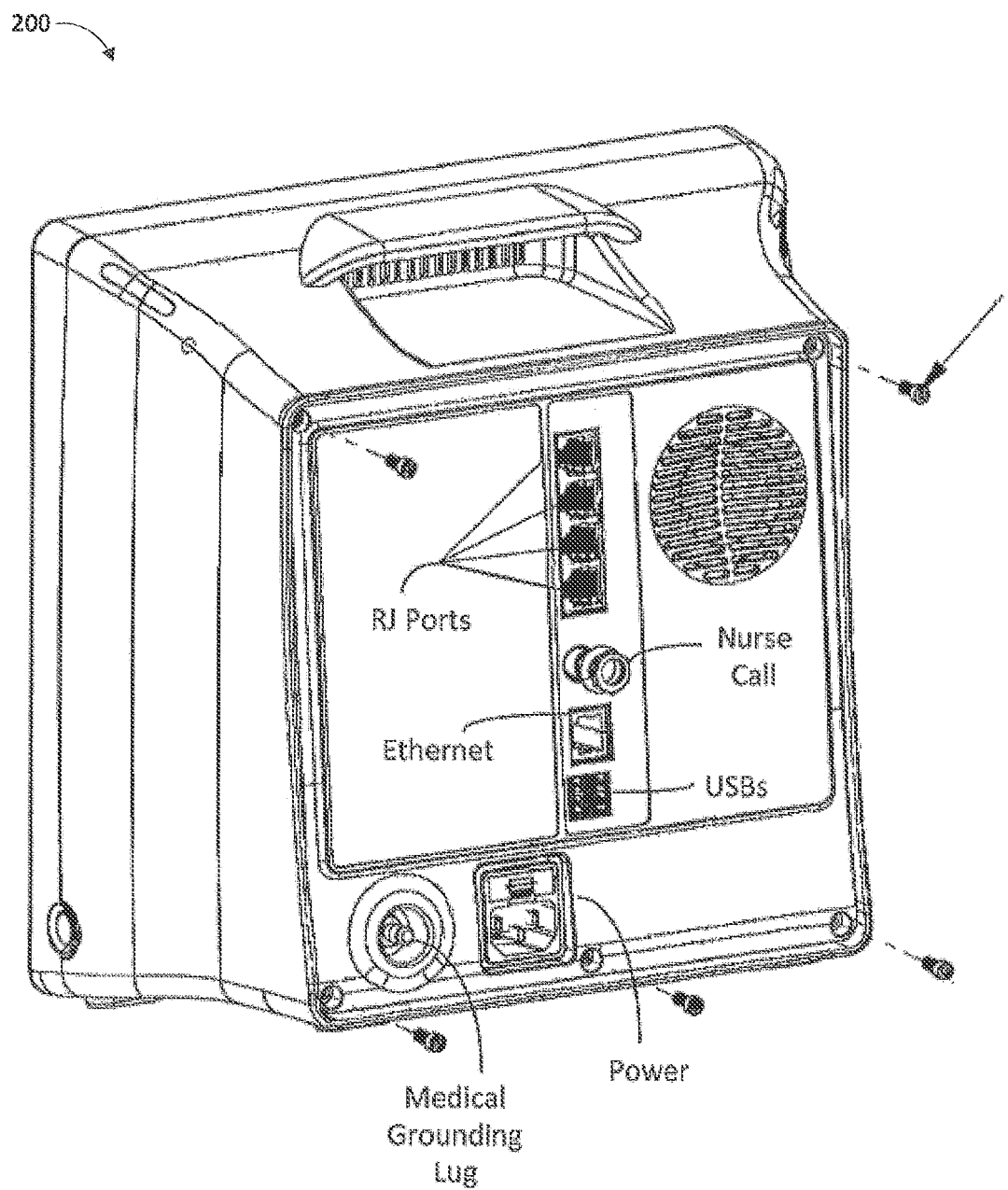
FIG. 2C illustrates a perspective view of the back side of the hub of FIG. 2B, according to certain embodiments.

FIG. 2C illustrates a perspective view of a back side of the patient monitoring device 300 of FIG. 2B, showing an exemplary serial data inputs. In an embodiment, the inputs include such as RJ 45 ports. As is understood in the art, these ports include a data ports similar to those found on computers, network routers, switches and hubs. In an embodiment, a plurality of these ports are used to associate and/or correlate data from various devices with the specific patient identified in the patient monitoring device 300. FIG. 2C also shows a speaker, the nurse call connector, the Ethernet connector, the USBs, a power connector and a medical grounding lug.

Figure 2D:
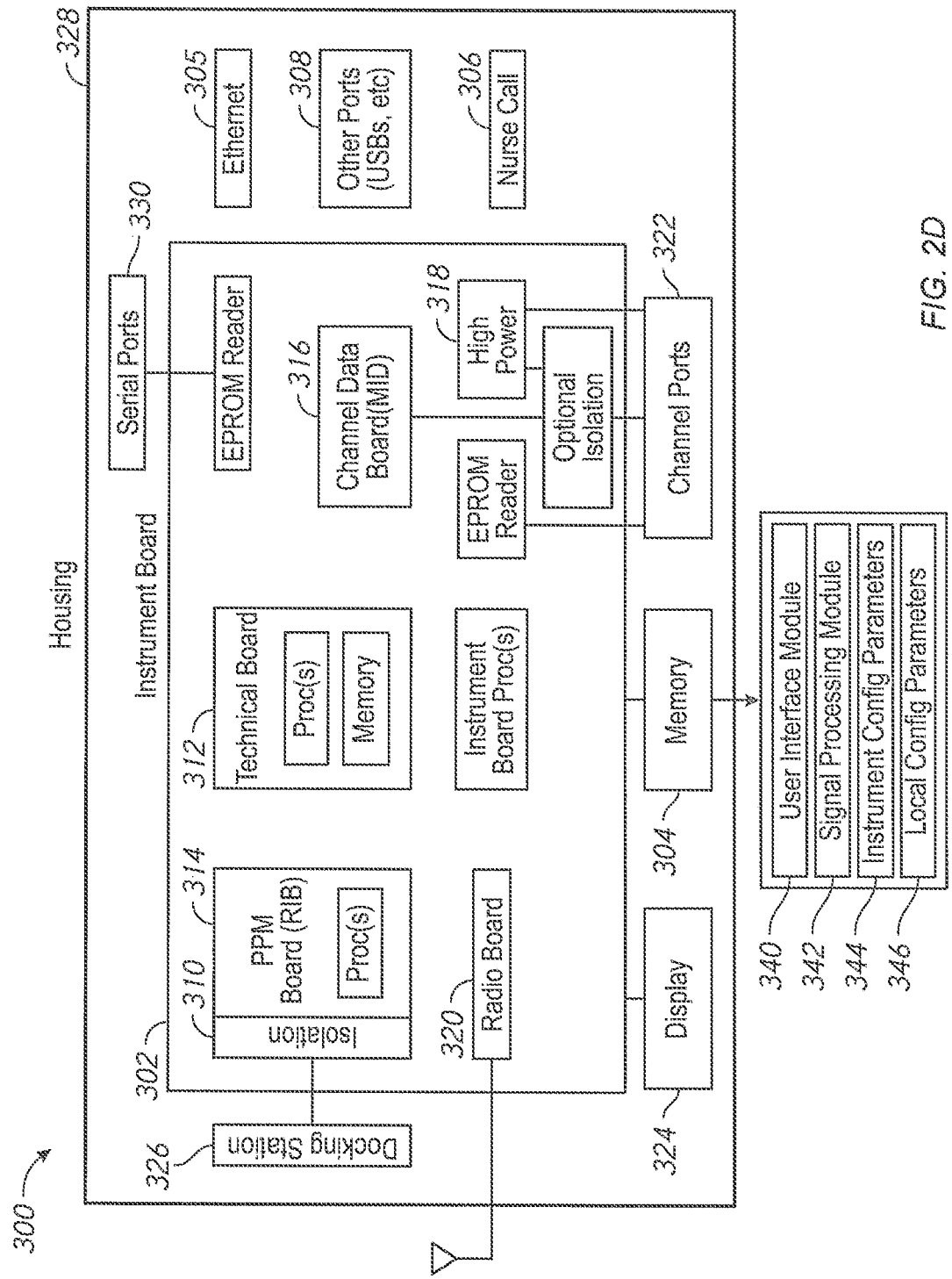
FIG. 2D illustrates a simplified exemplary hardware block diagram of the hub of FIG. 2B, according to certain embodiments.

FIG. 2D illustrates a simplified exemplary hardware block diagram of the patient monitoring device 300. As shown in FIG. 2D, the housing 328 of the patient monitoring device 300 positions and/or encompasses an instrument board 302, a core or technical board 312, the display 324, memory 304, and the various communication connections, including serial ports 330, channel ports 322, Ethernet ports 305, nurse call port 306, other communication ports 308 including standard USB, or the like, and a docking station interface 310. The instrument board 302 comprises one or more substrates including communication interconnects, wiring, ports and the like to enable the communications and functions described herein, including inter-board communications. The technical board 312 includes the main parameter, signal, and other processor(s) and memory. A portable monitor board ("RIB") 314 includes patient electrical isolation for the monitor 200 and one or more processors. A channel board ("MID") 316 controls the communication with the channel ports 322 including optional patient electrical isolation and power supply 318, and a radio board 320 includes components configured for wireless communications.

Additionally, the instrument board 302 and/or the technical board 312 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 and/or the technical board 312 may comprise a large number of electronic components organized in a large number of ways.

Because of the versatility needed to process many different physiological parameters, the technical board 312 further comprises a revision number or other indication of the circuit design and capabilities of a specific technical board 312.

Likewise, because of the versatility needed to display the processed physiological parameters for use by many different end users, the instrument board 302 further comprises a revision number or other indication of the circuit design and capabilities of the specific instrument board 302.

In an embodiment, the memory 304 comprises a user interface module 340, a signal processing module 342, instrument configuration parameters 344, and local configuration parameters 346.

The instrument board 302 accesses the user interface module 340 to process the waveforms, alerts, and alarms to provide indications of the waveforms, alerts, alarms or other data associated and/or correlated with the physiological parameters for the patient monitoring device 300. The technical board 312 accesses the signal processing module 342 to process the physiological information for the patient monitoring device 300.

Software for the patient monitoring device 300 is also subject to upgrading to increase its capabilities. The signal processing module 342 further comprises a version number or other indication of the code found in the specific signal processing module 342. Likewise, the user interface module 340 further comprises a version number or other indication of the code found on the specific user interface module 340.

In an embodiment, some or all of the serial numbers, the model numbers, and the revision numbers of the technical board 312 and the instrument board 302 that comprise the specific patient medical monitoring hub 300 are stored in the instrument configuration parameters 344. Further, the version numbers of the signal processing module 342 and the user interface module 340 are stored in the instrument configuration parameters 344. In an embodiment, the instrument configuration parameters 344 further comprise indications of the physiological parameters that are enabled, and indications of the physiological parameters that are capable of being enabled for the patient monitoring device 300.

In an embodiment, the local configuration parameters 346 comprise a location of the patient monitoring device 300 within the facility, an indication of whether the device is configured for adult or pediatric monitoring, and the like.

Figure 3A:
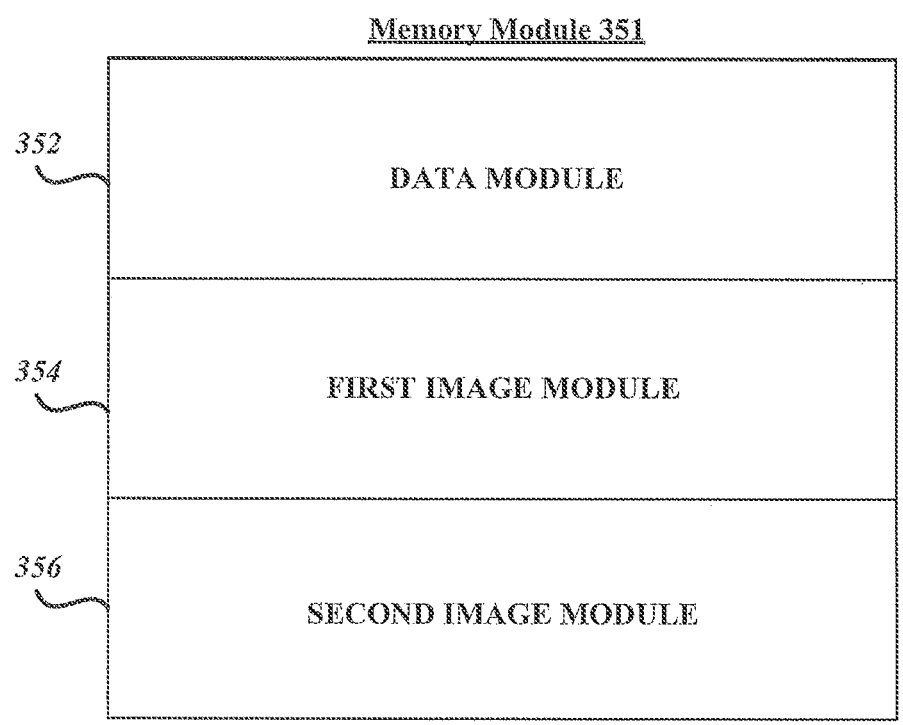
FIG. 3A is a diagram illustrative of an embodiment of a memory module of a processor of a patient monitor, according to certain embodiments.

In an embodiment, the patient monitoring device 300 comprises a Root® Patient Monitoring and Connectivity Platform by Masimo Corporation, Irvine, CA that includes the Radical-7® also by Masimo Corporation, Irvine, CA Memory FIG. 3A is a diagram illustrative of an embodiment of a memory module of a processor of a patient monitoring device 300. As illustrated, the memory module 351 is divided into a plurality of memory partitions. Each of the memory partitions can include one or more memory modules. For example, a partition can include a data module 352 or an image module 354, 356.

The image module can include a system image from which the processor can boot. In embodiments where the memory module 351 includes multiple image modules, the processor is capable of booting from more than one memory module partition. For example, as illustrated in FIG. 3A, the memory module 351 includes a first image module 354 and a second image module 356, and the processor may boot from either image module. While, in some instances, the first and second image module 354, 356 include the same image, generally these image modules include different images. Thus, in some embodiments, it can be advantageous for the processor to boot from a specific image module.

In a non-limiting example, the first image module 354 can include an old system image and the second image module 356 can include a new system image, such as a recent software upgrade. In some embodiments, it can be advantageous to boot from the second image module 356 because, for example, it includes an upgrade which may fix bugs or improve overall usability. However, in some embodiments, such as when the newest image upgrade is unproven or contains bugs, it can be advantageous to retain and boot from the first image module 354 which includes a system image which has been proven to work.

In some embodiments, the first image module 354 includes an original system image, such as the system image written by a manufacturer. In embodiments such as these, if the processor detects an error in an upgraded system image, it can boot from the original system image. However, due to memory constraints and because the original system image generally includes out of date features, it can be advantageous to re-write an image module including the original system image with an upgraded system image. For example, as described in more detailed with respect to FIGS. 3B and 3C, it can be advantageous for the memory module 351 to include at least two image modules.

Figure 3B:
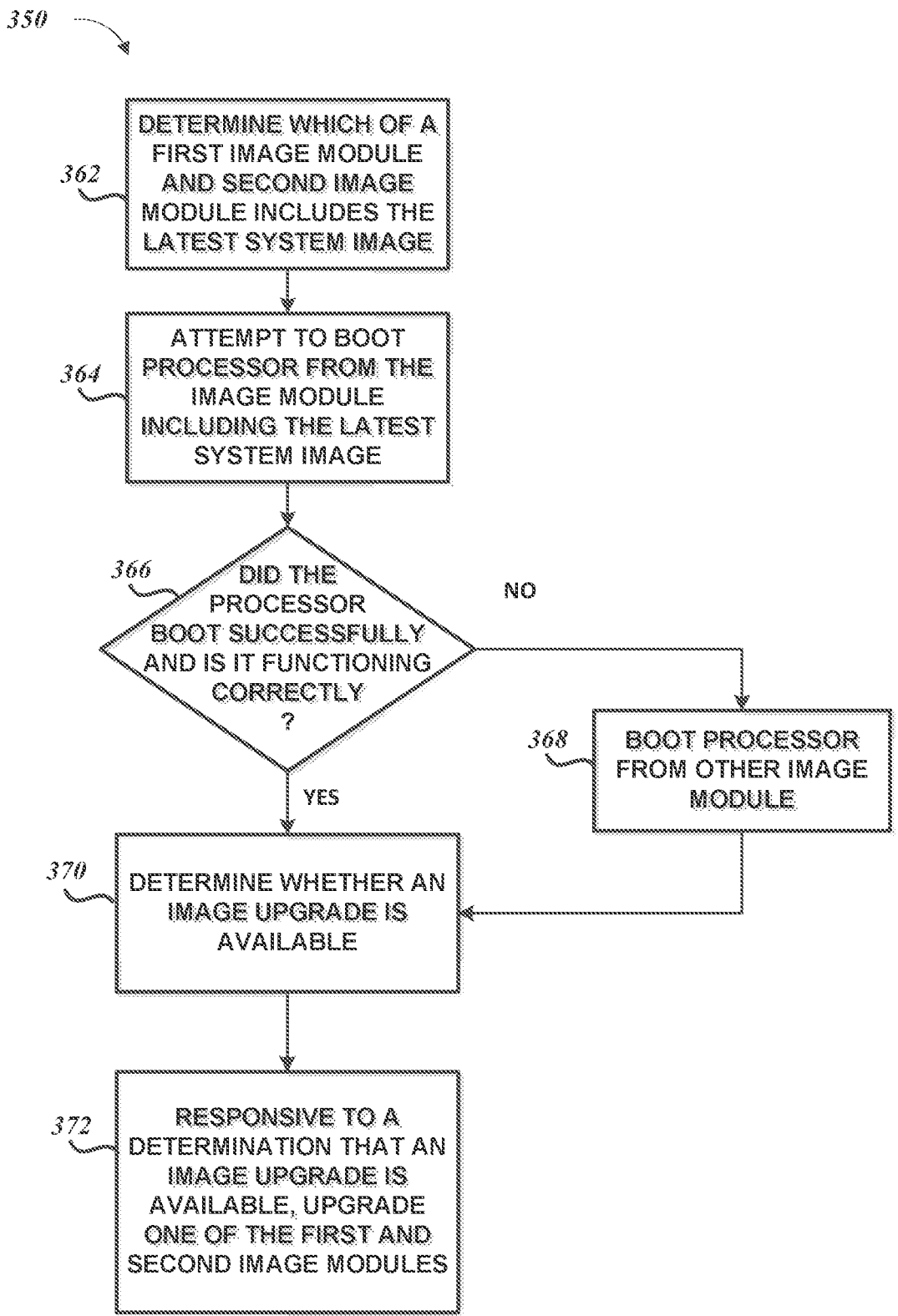
FIG. 3B is a flow diagram illustrative of an embodiment of a routine implemented by a processor having the memory module 351 of FIG. 3A, according to certain embodiments.

FIG. 3B is a flow diagram illustrative of an embodiment of a routine 350 implemented by a processor having the memory module 351 of FIG. 3A. However, it should be understood that a similar routine can be implemented on a processor having a memory module with more than two image modules.

At step 362, a processor determines which of the first and second image modules 354, 356 includes the latest system image. In some embodiments, the processor makes this determination based at least in part on a time stamp, a version number, or any other system image identifier. In some embodiments, the processor can make this determination based on which image module was most recently upgraded. In other embodiments, the patient monitoring system keeps track of which image module includes the latest system upgrade and the processor can access this information.

At step 364, the processor attempts to boot up from the image module including the latest system image. As described in more detail below with respect to step 372, the image module including the latest system image may be untested by this particular processor and may have bugs or download errors which prevent the processor from booting or operating properly. Accordingly, in some embodiments, the processor will not be able to boot from the image module including the latest system image or may determine that there is an operation error after boot up.

At step 366, the patient monitoring system, the processor, and/or another processor determines whether the processor successfully booted from the image module including the latest system image. In addition, even if the boot was successful, the functionality of the processor can be monitored to determine whether the processor is functioning correctly. In some embodiments, the functionality of the processor is monitored by another processor, such as a supervisor processor. In other embodiments, the processor can perform a self-check to determine whether it has full functionality. In some embodiments, the current attempt to boot from the image module including the latest system image is the first time the processor has attempted to boot from this system image. That is because the image module may have been upgraded the last time the processor was booted up. Accordingly, it can be important to test the current system image because a new upgrade may be available (see step 370) it is important to determine which image module, the first image module 354 or the second image module 356, should be upgraded with the available system upgrade. Further, if it is determined that a previous boot or operation of a new image contained an error or failed, the system can re-download the new image version and rewrite the image that contained the error.

At step 368, the processor either did not successfully boot from the image module including the latest system image or the processor was not functioning properly. Accordingly, the processor boot from another image module. In this example, because there memory module includes two image modules, the processor boots from the image module not used in step 364. However, it should be understood that the memory module can include more than two image modules.

At step 368, the processor knows it can boot from the older image module that has been used and tested on a previous occasion. Therefore, in some embodiments, booting from this image module is more reliable than booting from a different image module. In some embodiments, the functionality of the processor is not tested at this step. However, in other embodiments, the functionality of the processor is tested. For example, in some embodiments, the functionality of the processor is monitored by another processor.

At step 370, the processor, the patient monitoring system, and/or another processor determines whether an image upgrade exists and/or is available. In some embodiments, a processor of the patient monitoring system keeps track of which system images resides on the image modules and can compare that information to available image upgrades. In some embodiments, an image upgrade can be obtained wirelessly (such as downloaded from the internet) from a wired connection (such as an Ethernet connection, MOC-3 or a MOC-9 port), or from a removable memory via a USB port or other data port.

At step 372, responsive to a determination that an image upgrade is available, the processor upgrades one of the image modules. For instance, if the processor attempted and failed to boot from the image module including the latest system image, then the processor may write the image upgrade over the system image of that image module. Likewise, if the processor failed to function properly while after booting from a particular image module, then the processor can write the image upgrade over the system image of that image module. However, if the processor was able to boot and correctly function from the image module including the latest system image, then the processor can write the image upgrade over the system image of the image module having the older system image.

Figure 3C:
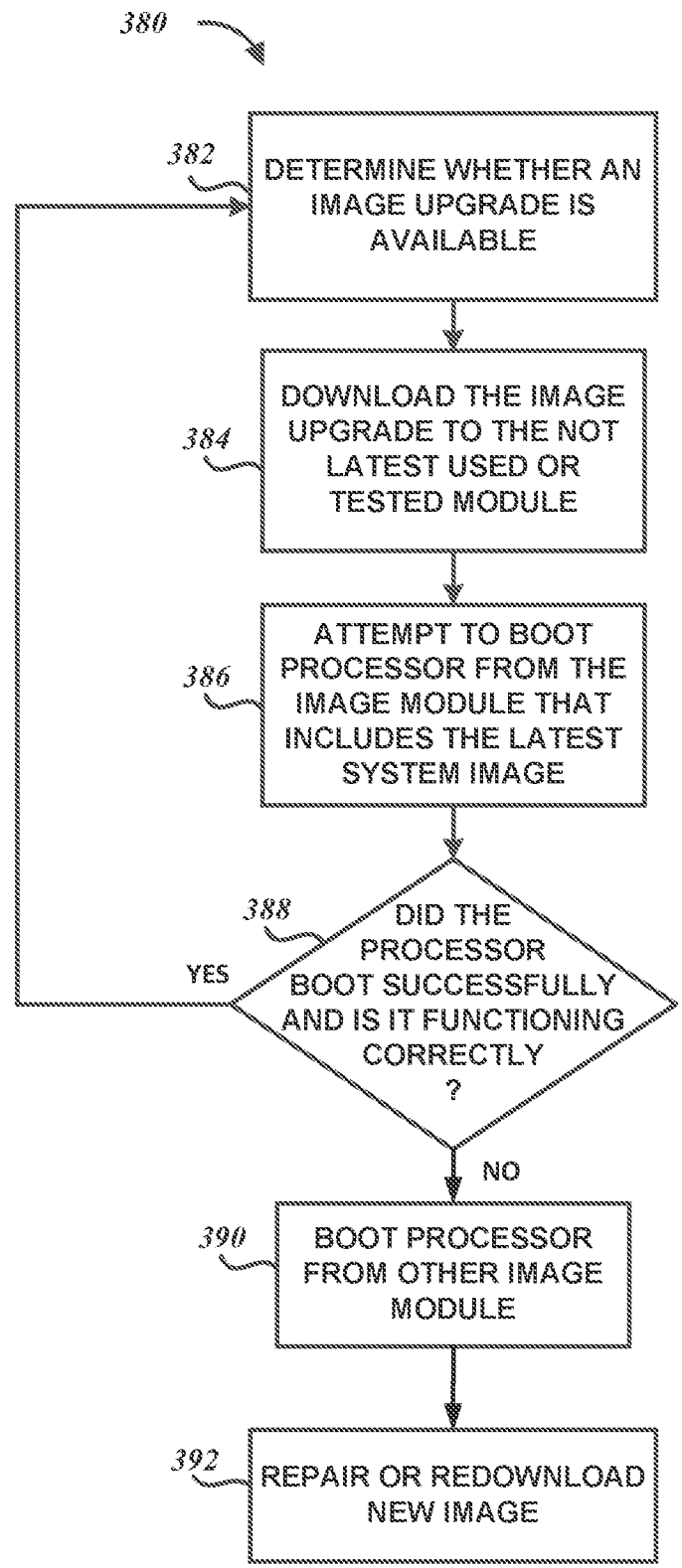
FIG. 3C is a flow diagram illustrative of another embodiment of a routine implemented by a processor having the memory module 351 of FIG. 3A, according to certain embodiments.

FIG. 3C is a flow diagram illustrative of another embodiment of a routine 380 implemented by a processor having the memory module 351 of FIG. 3A. However, it should be understood that a similar routine can be implemented on a processor having a memory module with more than two image modules or multiple processor having one or more image modules.

At step 382, the processor, the patient monitoring system, and/or another processor determines whether an image upgrade exists and/or is available. Any of the system processors can keep track of which system images resides on the image modules and can compare that information to available image upgrades. An image upgrade can be obtained, for example, wirelessly (such as downloaded from the internet) from a wired connection (such as an Ethernet connection, MOC-3 or a MOC-9 port), or from a removable memory via a USB port or other data port.

At step 384, responsive to a determination that an image upgrade is available, the processor upgrades the not latest used or tested module of the first and second image modules 354, 356. For example, the processor keeps track of which system images resides on the image modules 354, 356 and which image module 354, 356 includes a latest image and which image module 354, 365 includes the not latest, not tested, or older image.

The processor keeps track of which system image resides on the image modules 354, 356 based at least in part on a time stamp, a version number, or any other system image identifier. The processor can make this determination, for example, based on which image module 354, 356 was most recently upgraded. The patient monitoring system can also keep track of which image module 354, 356 includes the latest system upgrade and the processor can access this information.

At step 386, the processor attempts to boot up from the image module 354, 356 including the latest system image. The image module 354, 356 including the latest system image may be untested by this particular processor and may have bugs or download errors which prevent the processor from booting or operating properly. Accordingly, occasionally, the processor will not be able to boot from the image module 354, 356 including the latest system image or may determine that there is an operation error after boot up.

At step 388, the patient monitoring system, the processor, and/or another processor determines whether the processor successfully booted from the image module 354, 356 including the latest system image. In addition, even if the boot was successful, the functionality of the processor can be monitored to determine whether the processor is functioning correctly.

The functionality of the processor can be, for example, monitored by another processor, such as a supervisor processor. The processor can also or alternatively perform a self-check to determine whether it has full functionality. A current attempt to boot from the image module 354, 356 including the latest system image may be the first time the processor has attempted to boot from this system image. That is because the image module 354, 356 may have been upgraded the last time the processor was booted up. Accordingly, it can be important to test the current system image because a new upgrade may be available. It is important to determine which image module, the first image module 354 or the second image module 356, should be upgraded with the available system upgrade. Further, if it is determined that a previous boot or operation of a new image contained an error or failed, the system can re-download the new image version and rewrite the image that contained the error.

If, at step 388, the processor booted successfully and is operating correctly, the processor returns to step 382 to determine whether an image upgrade is available. If, at step 388, the processor does not boot successfully or is not operating correctly, the processor moves to step 390.

At step 390, the processor either did not successfully boot from the image module 354, 356 including the latest system image or the processor was not functioning properly. Accordingly, the processor boots from the other of the image module 354, 356. In the illustrated embodiment, memory module 351 includes two image modules 354, 356, and the processor boots from the image module 354, 356 that was not used in step 386.

At step 390, the processor knows it can boot from the older image module that has been used and tested on a previous occasion. Therefore, in some embodiments, booting from this image module is more reliable than booting from a different image module.

For example, if the processor determined that the memory module 354 included the updated system image, booted from image module 354, and determined that the boot was unsuccessful, then the processor will boot from image module 356. In this example, image module 356 is the not latest or used image module. Image module 356, in this example, is the older image module that has been used and tested.

The functionality of the processor may not be tested at step 390 as it is a known working image. However, in other embodiments, the functionality of the processor is tested. For example, in some embodiments, the functionality of the processor is monitored by another processor.

At step 392, the processor, the patient monitoring system, and/or another processor repairs or redownloads the new or upgraded image into the image module 354, 356 that failed at step 388. In the example above, image module 354 failed. The processor repairs the system image or redownloads a new or updated system image into image module 354. It should be understood that the memory module 351 can include more than two image modules 354, 356.

Accordingly, although the memory module 351 includes only two image modules 354, 356, the processor can always retain the ability to boot from a functioning system image, despite not having the original system image. As such, the image module having the older system image can act as a reliable backup system.

With respect to routines 300 and 350 illustrated in FIGS. 3B and 3C, respectively, the computer hardware can be further configured to determine whether the at least one patient monitoring device is actively monitoring, determine whether an override is enabled, download and/or boot from the upgraded image module in the at least one patient monitoring device during active monitoring when the override is enabled, and download and/or boot from the upgraded image module in the at least one patient monitoring device at a period of non-monitoring when the override is disabled.

Patient Monitoring Device (PMD) Management System

Figure 4:
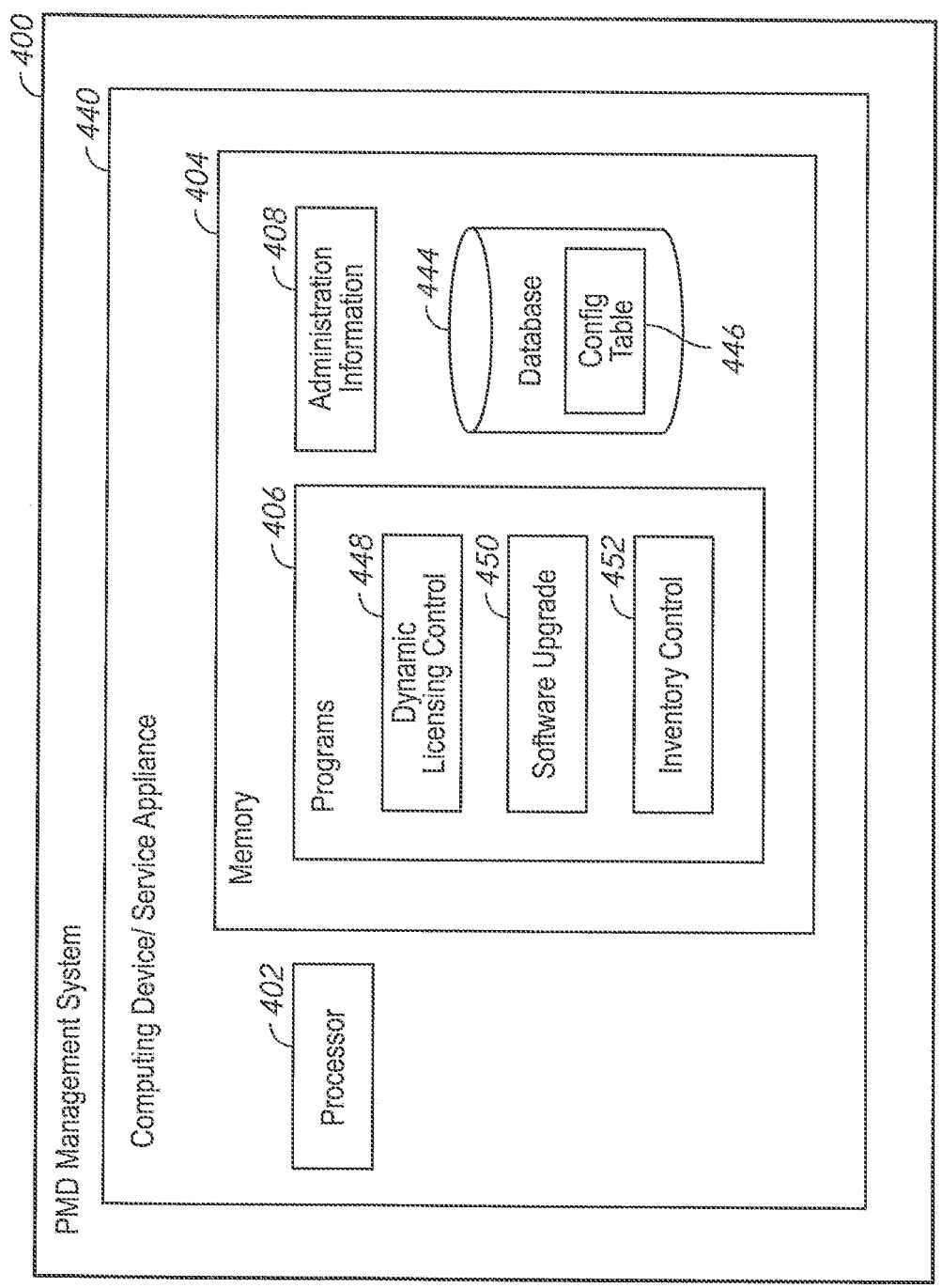
FIG. 4 is an exemplary block diagram of patient monitoring device management system, according to certain embodiments.

FIG. 4 is an exemplary block diagram of a patient monitoring device (PMD) management system 400. The PMD management system 400 is a computer-implemented management system that manages licenses, and updates software, and controls inventory for the patient monitoring environment.

The PMD management system 400 comprises a computing device or service appliance 440 that comprises a processor 402 and memory 404. The processor 402 can comprise controller circuitry, processor circuitry, processors, general-purpose single-chip or multi-chip microprocessors, digital signal processors, embedded microprocessors, microcontrollers, program logic, other substrate configurations representing data and instructions, and the like. In an embodiment, the service appliance 440 comprises a server.

In an embodiment, the PMD management system 400 comprises a digital processing system 400 that executes database schema to manage the patient monitoring devices 110, 200, 300 and sensors 202 in the patient environment, where the digital processing system 400 comprises a digital data processor and a server. In another embodiment, the PMD management system 400 comprises a digital database processor 400 that manages the patient monitoring devices 110, 200, 300 and sensors 202 in the patient environment.

The memory 404 comprises programs 406 such as a dynamic licensing control module 448 that is configured to enable patient monitoring devices to monitor previously unmonitored physiological parameters, an inventory control module 452 that is configured to order or generate alerts to order patient monitoring devices and accessories when the inventory becomes depleted, a software version control module 450 that is configured to at least upgrade the software residing on the patient monitoring devices in the active inventory, and the like. The memory 404 further comprises hospital administrator's information 408 associated with the hospital, and one or more databases 444. In an embodiment, the hospital administrator's information 408 comprises default information available on drop-down menus that make it easier for the hospital administrator to interact with the dynamic licensing control module 448, the inventory control module 452, and the software version control module 450.

In another embodiment, the hospital administrator's information 408 further comprises an administration section that comprises default values for different types of licenses, minimum inventory quantities, types of patient monitoring devices, types of sensors and the like. In an embodiment, the default values are pre-defined values.

The database 444 further comprises a configuration table 446 for the hospital. The hospital configuration table 446 includes information relating to the patient monitoring devices 110, 200, 300 and the sensors 202 for the hospital. This information is accessed by the dynamic licensing control module 448, the inventory control module 450, and the software version control module 452.

The memory 404 can comprise one or more logical and/or physical data storage systems for storing data 408, 446 and applications 448, 450, 452 used by the computing device 402. Each of the functional components of the PMD management system 400 may be implemented in program code executed by one or more general or special purpose computers.

In the context of the present disclosure, actions indicated as being taken by the PMD management system 400 are preferably performed by or through, as applicable, the service appliance 440 and its associated software components. In an embodiment, the service appliance 440 is in wired or wireless communication with the network bus 120, the Internet 150, and the terminal 142.

FIG. 5 is an exemplary database 500 used to dynamically manage patient monitoring devices 110, 200, 300 and sensors 202 in a patient monitoring environment. In an embodiment, the hospital configuration table 446 comprises the database 500.

In an embodiment, the database 500 comprises device information for each patient monitoring device 110, 200, 300 associated with the hospital. Examples of device information are, but not limited to, one or more of a device type, a device model number, a device serial number, a revision number of the technology board 216, 312 associated and/or correlated with the device, a revision number of the instrument board 214, 302 associated and/or correlated with the device, a version number of the signal processing module 222, 342 associated and/or correlated with the device, and a version number of the user interface module 220, 340 associated and/or correlated with the device.

In an embodiment, the device information comprises an override indication that indicates whether any of the processes, such as, for example, one or more of the dynamic licensing process 448, the inventory control process 450, and the software upgrade process 452 can continue when the patient monitoring device is active or actively monitoring a patient.

Further examples of device information are, but not limited to, an instrument configuration table comprising one or more instrument configuration parameters 1-n, and a local configuration table comprising one or more local configuration parameters 1-n associated and/or correlated with the device. In an embodiment, the local configuration parameters comprise a location within the facility and an indication of adult or pediatric.

In an embodiment, the device information further comprises license information associated and/or correlated with the device, such as, but not limited to a device license identifier or number, a duration of the device license that may include a start date and a stop date, and a location within the hospital or facility to which the device license pertains.

In another embodiment, the device information further comprises information associated and/or correlated with the sensors 202 assigned to the device, such as but not limited to one or more of a sensor type, a sensor model number, and a sensor serial number.

In an embodiment, the database 500 further comprises sensor information for each sensor 202 associated and/or correlated with the hospital. Examples of sensor information are, but not limited to, one or more of a sensor type, a sensor model number, and a sensor serial number. In an embodiment, the sensor information further comprises license information associated and/or correlated with the sensor, such as, but not limited to a sensor license identifier or number, a duration of the sensor license that may include a start date and a stop date, and a location within the hospital or facility to which the sensor license pertains. In another embodiment, the sensor information further comprises information pertaining to the patient monitoring devices 110, 200, 300 associated and/or correlated with the sensor, such as the serial number of the associated patient monitoring device.

Figure 6:
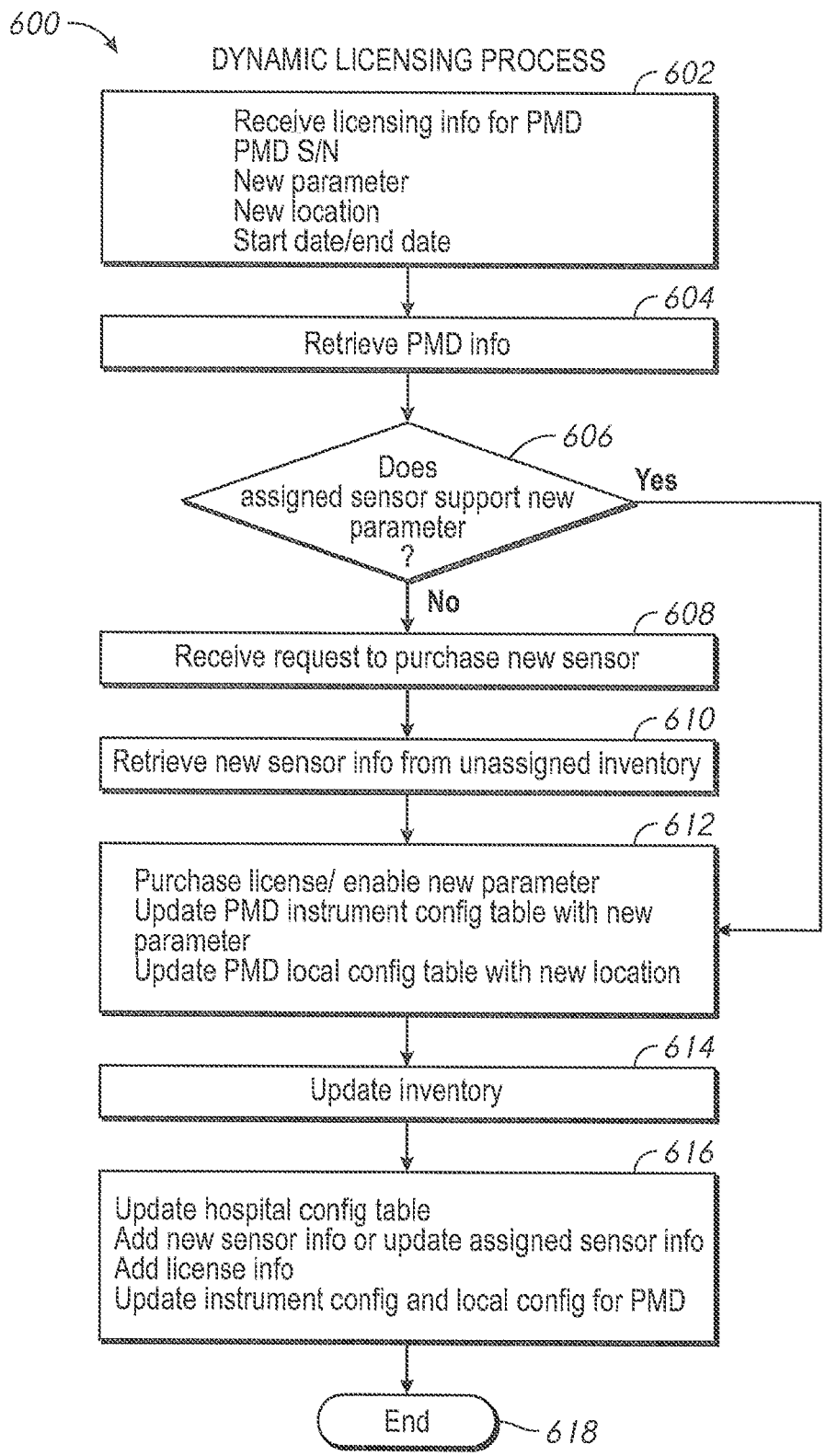
FIG. 6 is an exemplary flowchart showing a process for managing dynamic licenses for physiological parameters in a patient monitoring environment, according to certain embodiments.

FIG. 6 is a flowchart showing an exemplary process 600 for managing dynamic licenses for physiological parameters in a patient monitoring environment. In an embodiment, the licenses can be one or more of fixed licenses, floating licenses, licenses that can be purchased on the spot, licenses for a certain monitoring parameter, licenses for a fixed duration of time, pay-as-you-go licenses, proprietary licenses, term licenses, and the like.

In an embodiment, the dynamic licensing process 600 can tailor a license for the specific needs of the patient, care giver, and/or hospital administrator.

At step 602, the dynamic licensing process 600 receives licensing information for a selected patient monitoring device 110, 200, 300. For example, the received licensing information comprises one or more of the serial number of the patient monitoring device subject to the license, a new physiological parameter to be monitored, a location within the hospital to which the license pertains, a license duration, a start date, a stop date, type of license, such as a floating license, a pay-as-you-go license, a pay-as-you-go license, a proprietary license, a term license, and the like.

At step 604, the dynamic licensing process 600 retrieves the information associated and/or correlated with the selected patient monitoring device from the database 500. In an embodiment, the dynamic licensing process 600 provides access control for the patient monitoring device information.

At step 606, the dynamic licensing process 600 determines whether the assigned sensors associated with the selected patient monitoring device support the new parameter to be monitored.

If the new parameter is supported by the assigned sensor, the dynamic licensing process 600 moves to step 612. If the new parameter is not supported by the assigned sensor, the dynamic licensing process 600 moves to step 608, where the dynamic licensing process 600 notifies the administrator that the assigned sensor does not support the new parameter and receives the request to purchase a new sensor that supports the new parameter in response to the administrator notification.

At step 610, the dynamic licensing process 600 retrieves the sensor information associated and/or correlated with the new sensor. In an embodiment, the new sensor is from the stock inventory.

At step 612, the dynamic licensing process 600 causes the license to be purchased. In an embodiment, the dynamic licensing process 600 causes the license to be purchased by enabling the new parameter for the selected device. In an embodiment, enabling the new parameter comprises updating the instrument configuration table 224, 344 of the selected patient monitoring device to include the new parameter and updating the local configuration table 226, 346 of the selected patient monitoring device with the license location. In an embodiment, the dynamic licensing process 600 creates an electronic licensing agreement to monitor the new parameter for the monitoring duration and/or in the monitoring location. In an embodiment, the licensing agreement and the amount of the licensing fee are automatically sent to the responsible party associated with the patient.

At step 614, the dynamic licensing process 600 updates the hospital inventory for any sensors 202 removed from the inventory to fulfill the licensing requirements. In an embodiment, updating the inventory comprises performing an embodiment of the inventory control process 452.

At step 616, the dynamic licensing process 600 updates the hospital configuration table 146, 446 with the sensor information associated and/or correlated with the sensor assigned to monitor the new parameter, adds or revises the device and sensor licensing information, and updates the instrument configuration table and the local configuration table for the selected patient monitoring device in the database 500. The dynamic licensing process 600 ends at step 618.

In another embodiment, the patient monitoring device (PMD) management system 400 further manages billing for licenses, patient monitoring devices 110, 200, 300, and sensors 202 in the patient monitoring environment. For example, the dynamic licensing process 600 is configured to monitor pay-as-you go licenses and send information such as license start date, license stop date, and license duration to a billing program. In another example, the dynamic licensing process 600 keeps track of the pay-for use licenses and sends information such as the number of uses of a sensor and/or a patient monitoring device and/or license to a billing program. In another embodiment, the dynamic licensing process 600 generates the billing statements.

Figure 7:
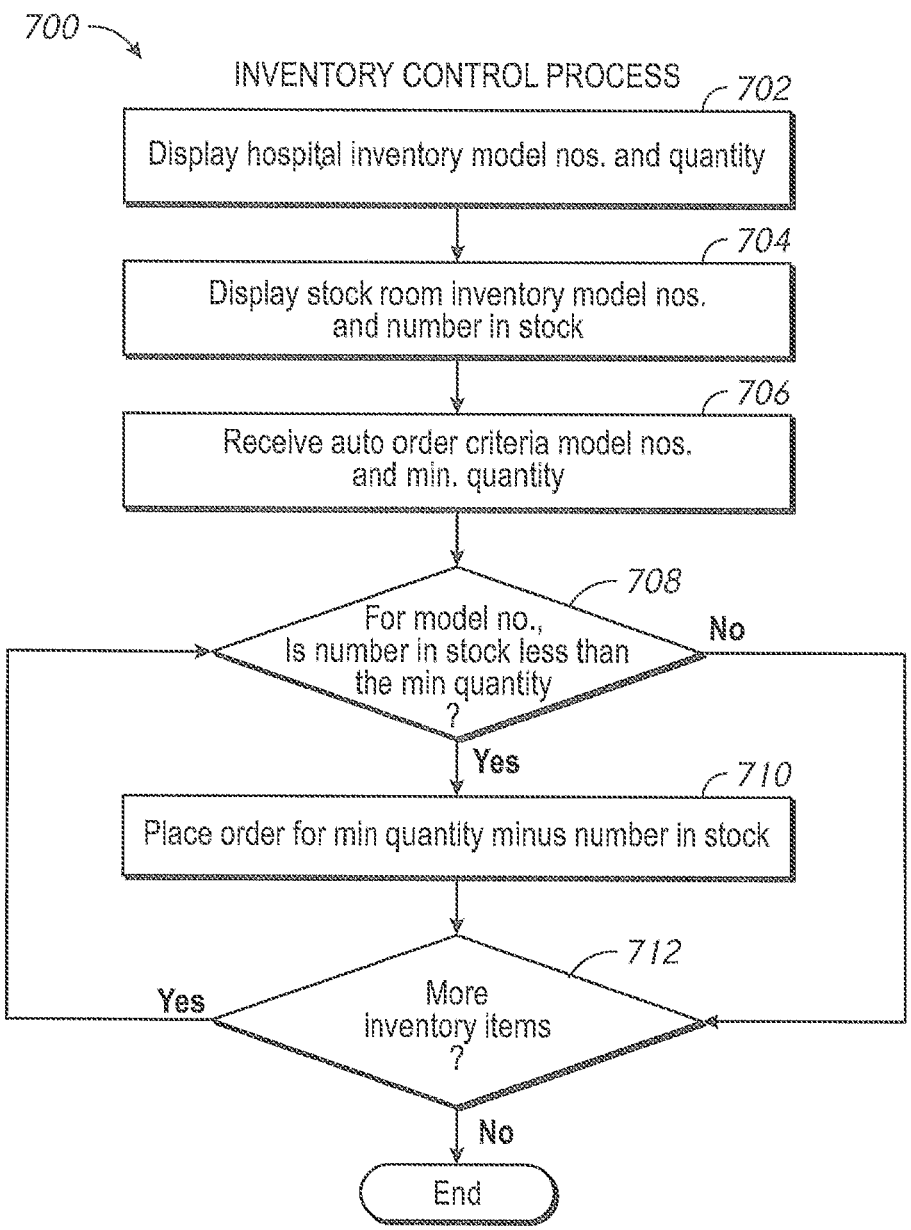
FIG. 7 is an exemplary flowchart showing an inventory control and auto-order process for patient monitoring equipment in a patient monitoring environment, according to certain embodiments.

FIG. 7 is a flowchart showing an exemplary inventory control and auto-order process 700 for the hard and soft inventory associated and/or correlated with the patient monitoring devices in a patient monitoring environment. Examples of the hard inventory include, but are not limited to patient monitoring devices 110, 200, 300, sensors 202, instrument boards 214, 302, and technical boards 216, 312. Examples of the soft inventory include but are not limited to software, such as software versions, software upgrades, and uploadable software, licenses, floating licenses, fixed licenses, and licenses available for on-the-spot purchasing.

For example, a floating license is a license that is available in limited numbers that is shared among a larger number of users over time. It is re-usable and can be held in a license pool, such as an inventory license pool. The inventory can include license pools having a floating quantity of licenses available and the floating quantity of available licenses can be decremented when a floating license is taken and incremented when a floating license is returned to inventory. A fixed license is assigned to one entity. In an embodiment, once a fixed license is used, the license count is decreased and it cannot be reassigned. The inventory can include fixed licenses having a fixed number of licenses available which is decremented when a license is taken.

At step 702, the inventory control process 700 displays the hospital inventory, including the model numbers and quantity for the hospital's patient monitoring devices 110, 200, 300 and the hospital's sensors 202. In an embodiment, the hospital inventory includes licenses in the hospital for the patient monitoring devices 110, 200, 300 and sensors 202. In an embodiment, the administrator's terminal 142 displays the hospital inventory.

At step 704, the inventory control process 700 further displays the hospital's stock room inventory, including the model numbers and quantity for the hospital's patient monitoring devices 110, 200, 300 and the hospital's sensors 202 that are stored in the stock room, or in other words, that are not assigned to be monitoring physiological parameters of a patient. In an embodiment, the hospital's stock room inventory includes licenses for the patient monitoring devices 110, 200, 300 and sensors 202 that are available for licensing. In an embodiment, the administrator's terminal 142 displays the stock room inventory.

At step 706, the process 700 receives auto-order criteria. In an embodiment, the hospital administrator enters the auto-order criteria on the administrator's terminal 142. In an embodiment, the auto-order criteria comprises model numbers of patient monitoring devices 110, 200, 300 and sensors 202 and a minimum quantity of these patient monitoring devices 110, 200, 300 and sensors 202 to have available in the stock room. In an embodiment, the auto-order criteria comprise minimum quantities of licenses for the sensors 202 and the patient monitoring devices 110, 200, 300 that are to be kept in the inventory.

At step 708, the inventory control process 700 determines whether the number in stock of a first model number is less than the minimum quantity of the first model number. When the number in the stock inventory is greater than the minimum quantity of the first model number, the inventory control process 700 moves to step 712.

When the number in the stock inventory is less than the minimum quantity, the inventory control process 700 moves to step 710, where the inventory control process 700 automatically places an order for a quantity of the first model number. In an embodiment, the inventory control process 700 orders the minimum quantity less the number in the stock inventory.

At step 712, the inventory control process 700 determines whether there are more inventory items. When there are more inventory items, the inventory control process 700 moves to step 708 and repeats steps 708-712 for the next inventory item. When there are no more inventory items, the inventory control process 700 ends at step 714.

In an embodiment, the inventory control process 700 further comprises adjusting the inventory numbers when an inventory item, such as a patient monitoring device 110, 200, 300, a sensor 202, or a license, for example, is returned or pushed back to the inventory. For example, once a sensor 202 is decommissioned, the sensor hardware can be returned to the inventory, the license for the sensor can be pushed back into the inventory, and the quantities stored in inventory can be adjusted upwards, accordingly.

Figure 8A:
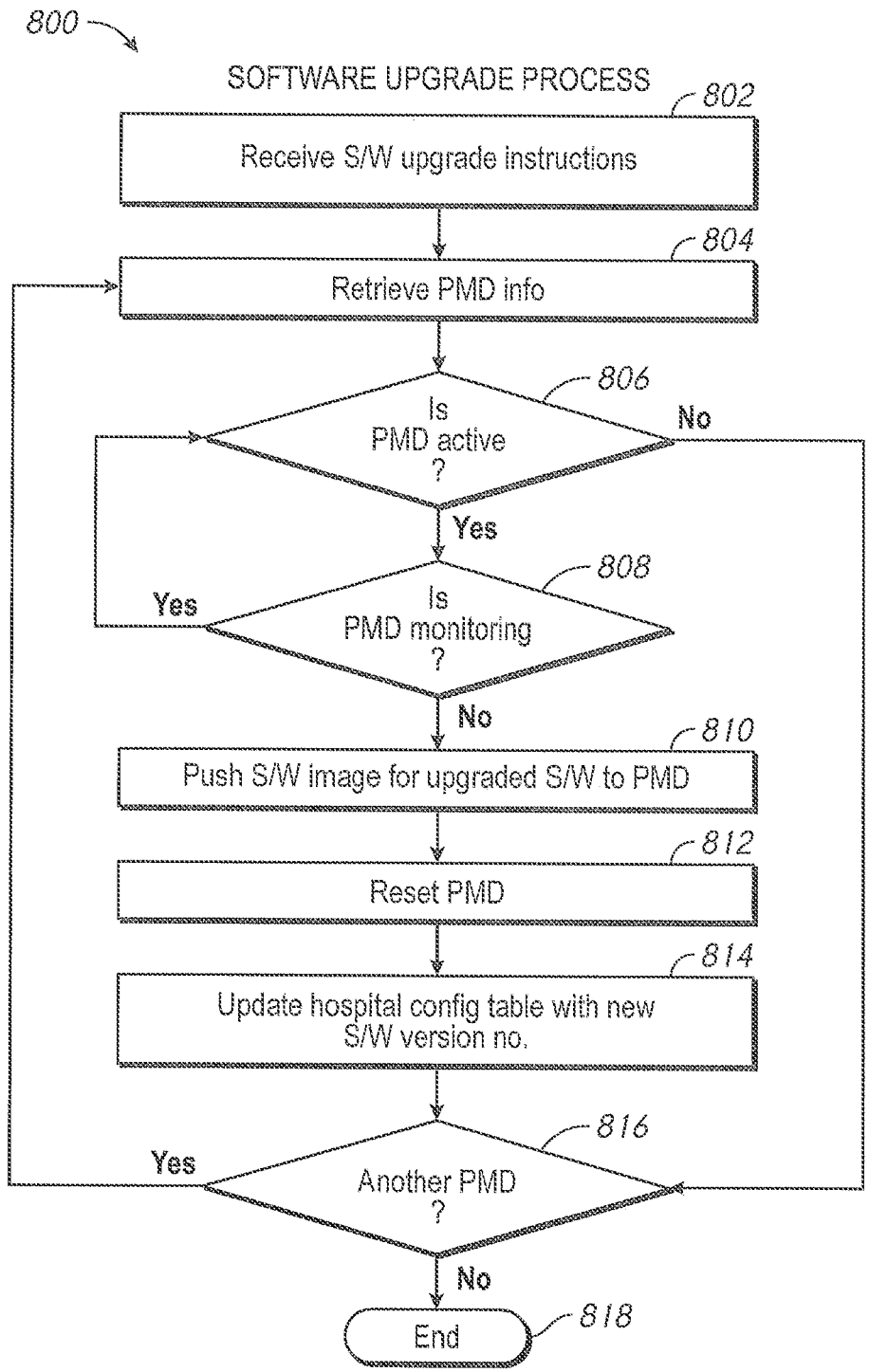
FIG. 8A is an exemplary flowchart showing a software version control process for patient monitoring equipment in a patient monitoring environment, according to certain embodiments.

FIG. 8A is a flowchart showing an exemplary software version control process 800 for patient monitoring devices in a patient monitoring environment. At step 802, the software version control process 800 receives software upgrade instructions. In an embodiment, the software upgrade instructions comprise the software version numbers for device model numbers. In an embodiment, the software version numbers are associated and/or correlated with revised software for one or more of the sensor 202, the user interface module 220, 340 and the signal processing module 222, 342.

At step 804, the software version control process 800 retrieves the device information for a first patient monitoring device. In an embodiment, the process 800 accesses the database 500 for the device information.

At step 806, the software version control process 800 determines whether the first patient monitoring device is active. In an embodiment, the patient monitoring device needs to be in communication with one or more of the hospital backbone 120, the Internet 150, and the service appliance 140, 440 to receive a software upgrade.

When the device is inactive, the software version control process 800 moves to step 816, where the process 800 determines whether there is another device.

When the device is active, the software version control process 800 moves to step 808, where the software version control process 800 determines whether the device is monitoring.

When the device is monitoring, the software version control process 800 loops between steps 806 and 808 until the device is no longer monitoring to assure that here is no interruption in the patient's monitoring.

At step 810, the software version control process 800 pushes the software image for the upgraded software to the patient monitoring device 110, 200, 300. At step 812, the software version control process 800 resets the patient monitoring device 110, 200, 300, and at step 814, the software version control process 800 updates the hospital configuration table 146/database 500 with the new software version numbers for the updated patient monitoring device 110, 200, 300.

At step 816, the software version control process 800 determines whether there are more patient monitoring devices 110, 200, 300 to upgrade. When there are additional devices, the software version control process 800 moves to step 804, where steps 804-816 are repeated for the next device. When there are no more devices to upgrade, the software version control process 800 ends at step 818.

Figure 8B:
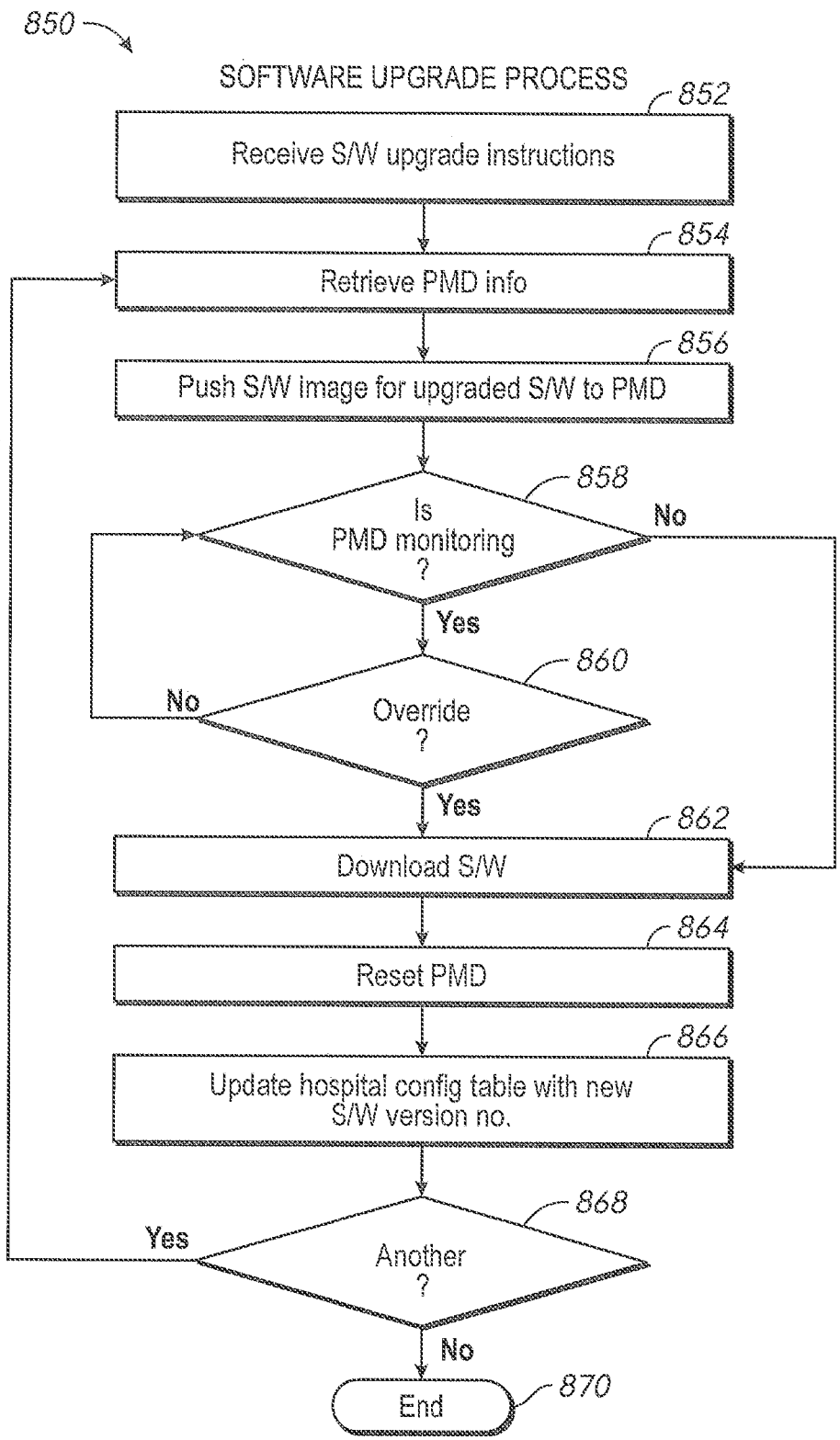
FIG. 8B is an exemplary flowchart showing another software version control process for patient monitoring equipment in a patient monitoring environment, according to certain embodiments.

FIG. 8B is a flowchart showing an exemplary software version control process 850 for patient monitoring equipment in a patient monitoring environment. At step 852, the software version control process 850 receives software upgrade instructions. In an embodiment, the software upgrade instructions comprise the software version numbers for device model numbers. In an embodiment, the software version numbers are associated and/or correlated with revised software for one or more of the sensor 202, the user interface module 220, 340 and the signal processing module 222, 342.

At step 854, the software version control process 850 retrieves the device information for a patient monitoring device or sensor. In an embodiment, the process 850 accesses the database 500 for the device information.

At step 856, the software version control process 850 pushes the software image for the upgraded software to the sensor 202 or patient monitoring device 110, 200, 300.

At step 858, the software version control process 850 determines whether the sensor 202 or the patient monitoring device 110, 200, 300 is active. In an embodiment, the patient monitoring device is in communication with one or more of the hospital backbone 120, the Internet 150, and the service appliance 140, 440 in order to receive a software upgrade.

When sensor 202 or the patient monitoring device 110, 200, 300 is not actively monitoring a patient, the software version control process 850 moves to step 862. When the sensor or patient monitoring device 110, 200, 300 is actively monitoring, the software version control process 850 moves to step 860 to determine whether override has been selected. In an embodiment, the software version control process 850 checks the device information retrieved in step 854. In an embodiment, the override indication is determined by the hospital administrator. In another embodiment, the override is approved before the software version control process 850 begins.

When override is not enabled, the software version control process 850 moves to step 858 and loops between steps 858 and 860 until the sensor 202 or patient monitoring device 110, 200, 300 is available to receive the software upgrade. When the override is enabled, the software version control process 850 moves to step 862.

At step 862, the software version control process 850 downloads the software image into the sensor 202 or patient monitoring device 110, 200, 300.

At step 864, the process 850 resets the sensor 202 or the patient monitoring device 110, 200, 300 to permit the sensor 202 or the patient monitoring device 110, 200, 300 to run the downloaded software, and at step 866, the software version control process 850 updates the hospital configuration table 146/database 500 with the new software version numbers for the updated sensor 202 or the patient monitoring device 110, 200, 300.

At step 868, the software version control process 850 determines whether there are more sensors 202 or patient monitoring devices 110, 200, 300 to upgrade.

In an embodiment, multiple devices can be upgraded in parallel. For example, the hospital can be divided into domains and all of the patient monitoring devices 110, 200, 300 in the selected domain can be software upgraded at the same time, at approximately the same time, or in parallel. Examples of domains within a hospital are floors of the hospital, units of the hospital such as the intensive care unit (ICU) and the neonatal unit, and the like.

In an embodiment, the sensors 202 and/or patient monitoring devices 110, 200, 300 in more than one domain can be software upgraded in parallel. In another embodiment, all of the patient monitoring devices in the hospital can be software upgraded in parallel. In further embodiments, more than one domain across more than one hospital can be software upgraded in parallel. In a further embodiment, all of the patient monitoring devices in multiple hospitals can be software upgraded in parallel.

Providing software upgrades to multiple patient monitoring devices in parallel or approximately simultaneously advantageously saves considerable time, effort, and expenses. For example, performing the software upgrade for the patient monitoring devices in one hospital manually took three people three days whereas one person at the hospital administrator terminal upgraded the hospital's patient monitoring device in 10 minutes using an embodiment of the software upgrade process 800, 850 described herein.

When there are additional sensors 202, patient monitoring devices 110, 200, 300, or additional groups of sensors/patient monitoring devices, the software version control process 850 moves to step 854 where steps 854-868 are repeated. When there are no more devices to upgrade, the software version control process 850 ends at step 870.

FIGS. 9A-9D are exemplary screen shots illustrating the processes of FIGS. 6-8. In an embodiment, the screen shots are displayed in the administrator's terminal 142.

Figure 9A:
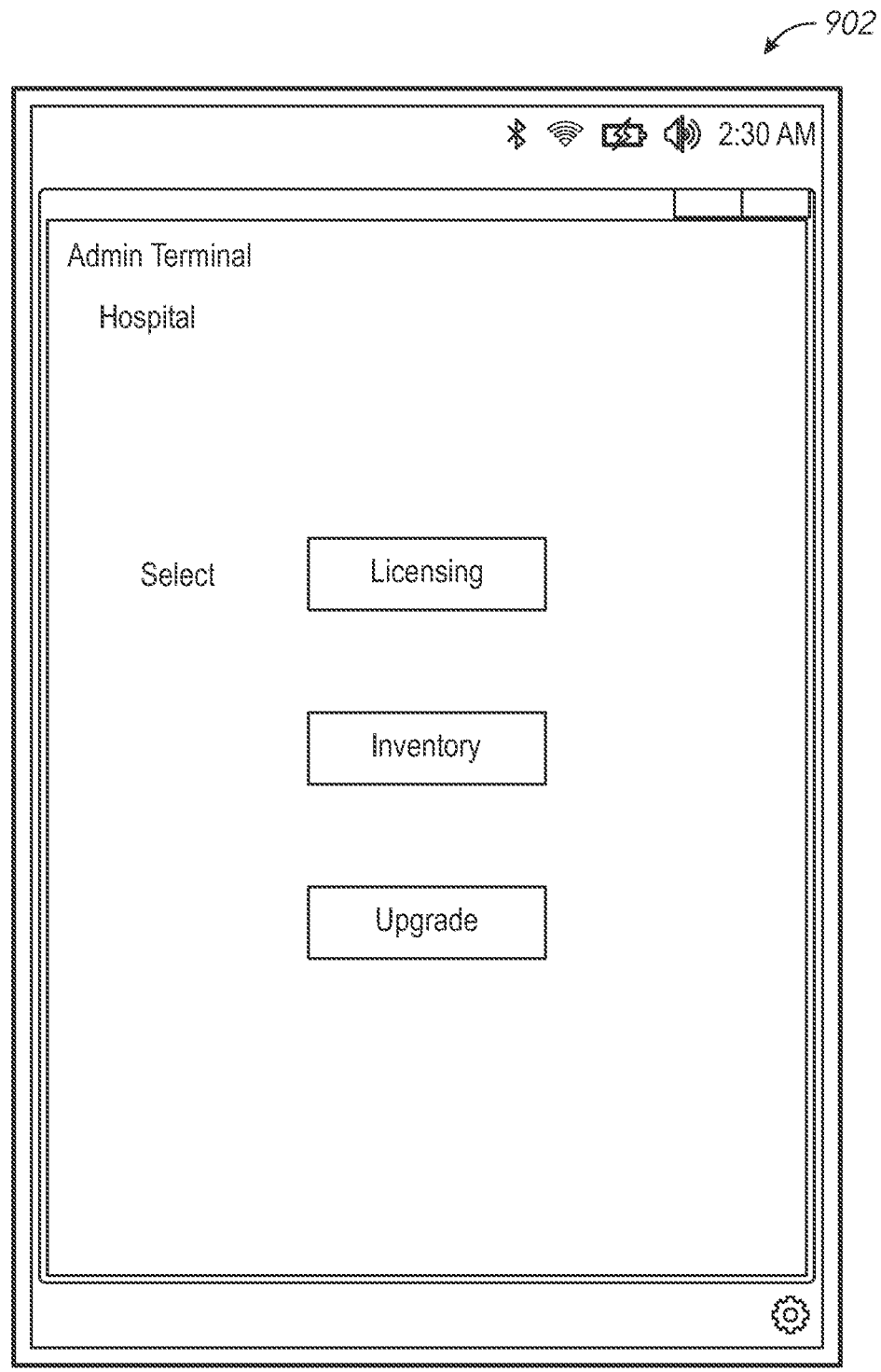
FIGS. 9A-9D are exemplary screen shots illustrating the processes of FIGS. 6, 7, 8A and 8B, according to certain embodiments.

FIG. 9A is an exemplary selections screen 902 showing the licensing, inventory, and upgrade selections available to the administrator.

Figure 9B:
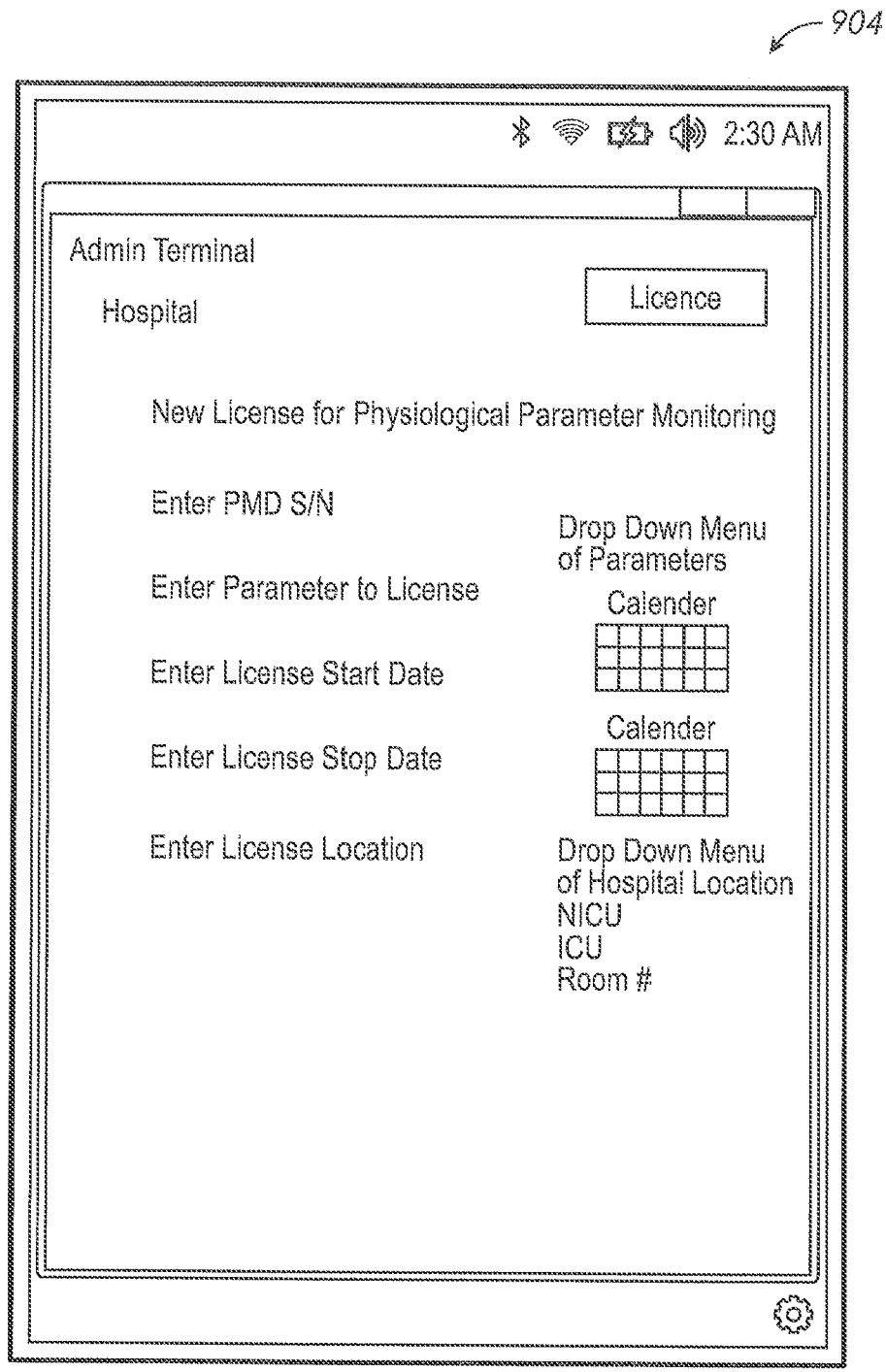

FIG. 9B is an exemplary license request screen 904 showing licensing parameters.

Figure 9C:
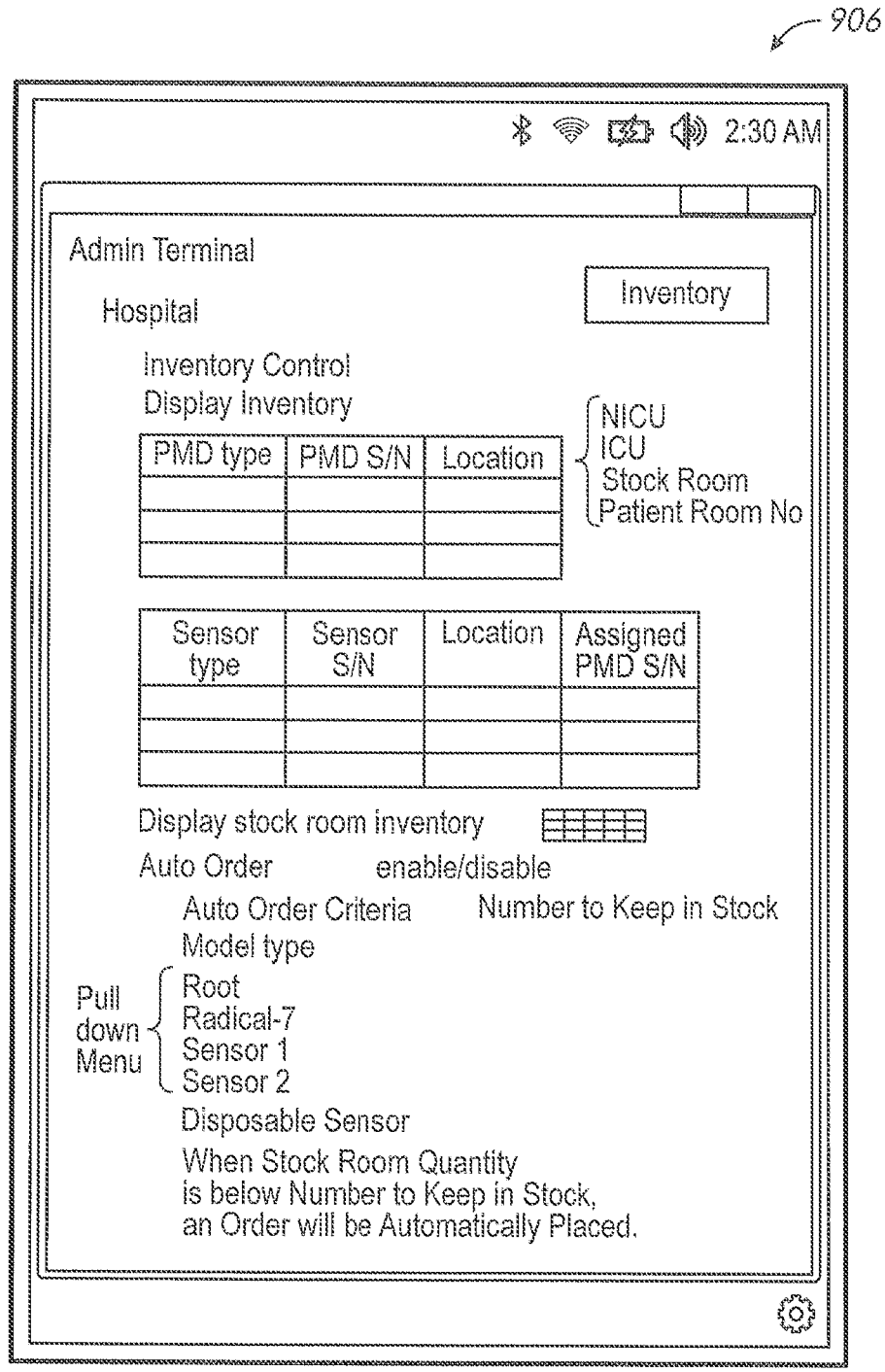

FIG. 9C is an exemplary inventory control and auto-order screen 906 displaying the hospital inventory and the stock room inventory. The inventory control and auto-order screen 906 further permits the administrator to enter the auto-order criteria for automatic ordering of patient monitoring devices 110, 200, 300 and sensors 202.

Figure 9D:
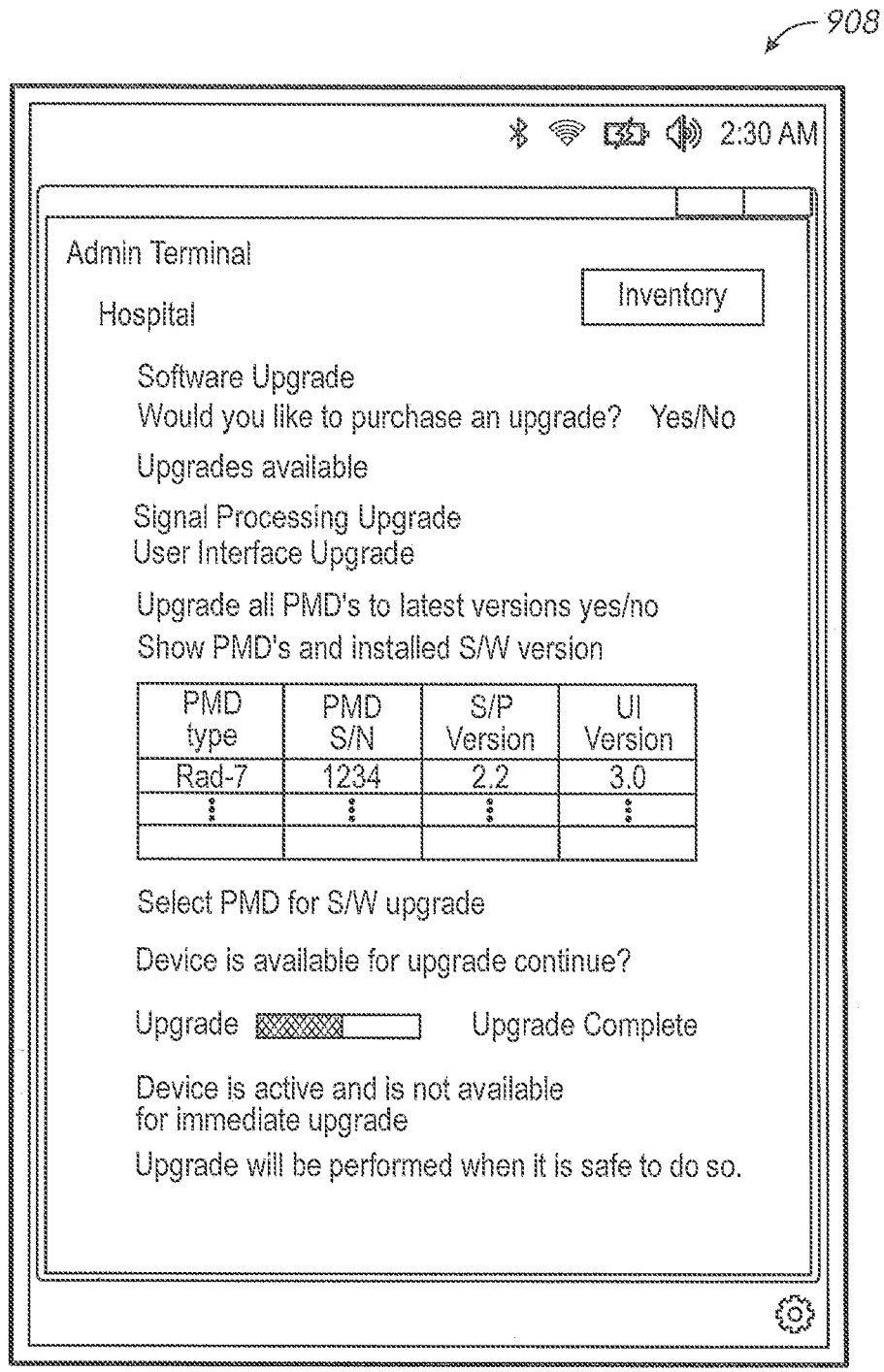

FIG. 9D is an exemplary software upgrade screen 908 displaying the board revision numbers and the software version numbers for the patient monitoring devices 110, 200, 300 in the hospital's inventory. The software upgrade screen 908 further permits the administrator to select patient monitoring devices 110, 200, 300 and sensors 202 for software upgrades.

Figure 10:
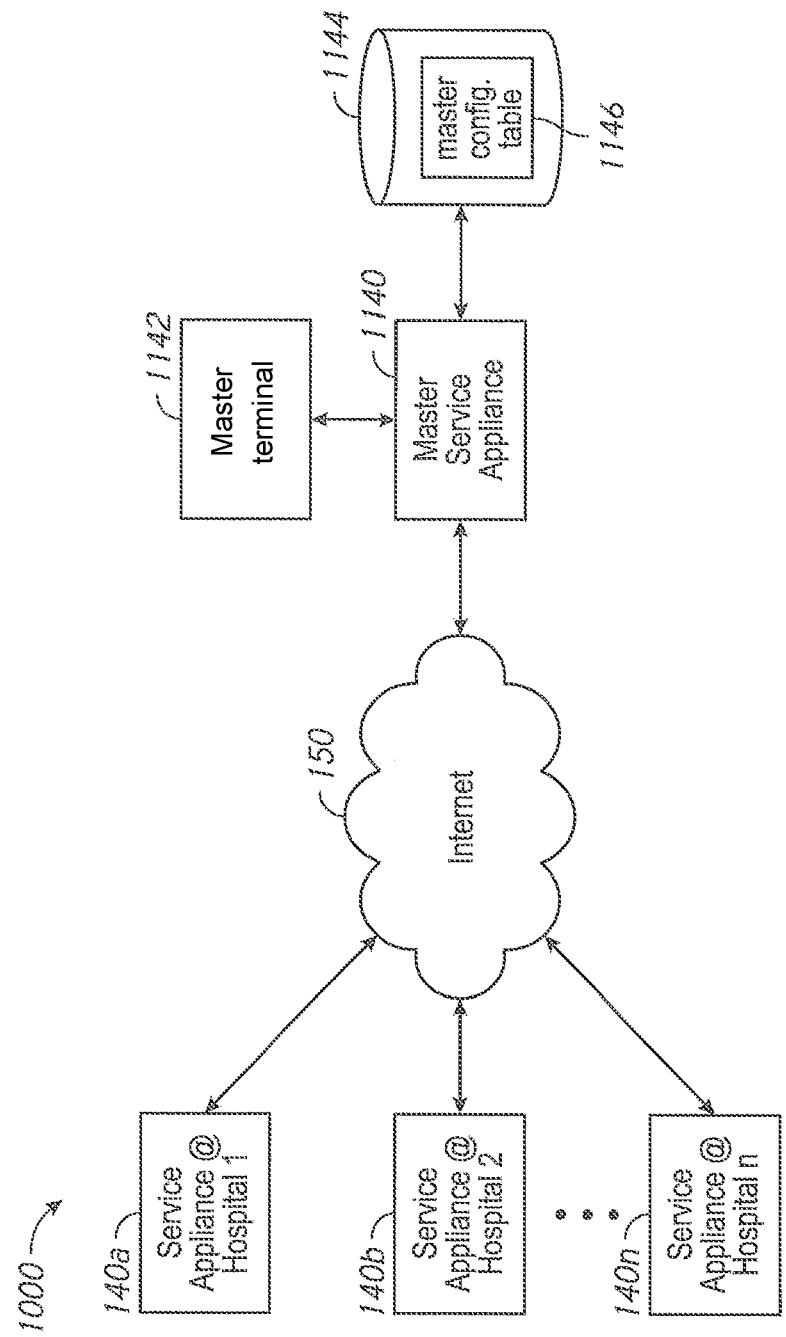
FIG. 10 is an exemplary block diagram showing a system to dynamically control multiple patient monitoring environments, according to certain embodiments.

FIG. 10 is an exemplary block diagram showing a system 1000 to manage multiple patient monitoring environments, according to certain embodiments of the disclosure. The system 1000 comprises a master service appliance 1140 in communication with a plurality of hospital service appliances 140a, 140b, ..., 140n via the Internet 150. Service appliance 140a is associated with the patient monitoring system of a first hospital and accesses the configuration table for the first hospital. Similarly, service appliance 140b is associated with the patient monitoring system of a second hospital and accesses the configuration table for the second hospital. And service appliance 140n is associated with the patient monitoring system of an $n^{th}$ hospital and accesses the configuration table for the $n^{th}$ hospital. In an embodiment, the master service appliance 1140 comprises a server.

The service appliance 1140 comprises a master licensing control system that is configured to monitor and interact with the dynamic licensing control processes 448 of the plurality of hospital service appliances 140a-140n. The service appliance 1140 further comprises a master inventory control system that is configured to monitor and interact with the inventory control and auto-order processes 450 of the plurality of hospital service appliances 140a-140n. The service appliance 1140 further comprises a master software version control system that is configured to monitor and interact with the software upgrade processes 450 of the plurality of hospital service appliances 140a-140n.

The system 1000 further comprises a master terminal 1142 and a storage device 1144. The service appliance 1140 is in wired or wireless communication with the Internet 150, the master terminal 1142, and the storage device 1144.

The storage device 1144 comprises a master configuration table 1146 for the plurality of hospitals. The master configuration table 1146 includes information relating to the patient monitoring devices 110, 200, 300 and the sensors 202 for each hospital of the plurality of hospitals. This information is accessed by the master licensing control system, the master inventory control system, and the master software version control system.

In an embodiment, the master terminal 1142 comprises user interface hardware, such as, but not limited to a keyboard, a mouse, and a monitor, that permit the user to interface with at least the master licensing control system, the master inventory control system, and the master software version control system.

FIG. 11 is an exemplary database structure 1100 used to dynamically manage patient monitoring devices 110, 200, 300 and sensors 202 in multiple patient monitoring environments. In an embodiment, the master configuration table 1446 comprises the database 1100. In an embodiment, the database 1100 comprises device information, as described above with respect to FIG. 5, for each patient monitoring device 110, 200, 300 associated with each hospital 1-$n$. The database 1100 further comprises a hospital identifier associated and/or correlated with the device information for the identified hospital. In an embodiment, the hospital identifier comprises one or more of the hospital name, hospital address, hospital location, an alpha numeric identifier, an identifying number, a PIN, or other unique information to identify the hospital.

Figure 12:
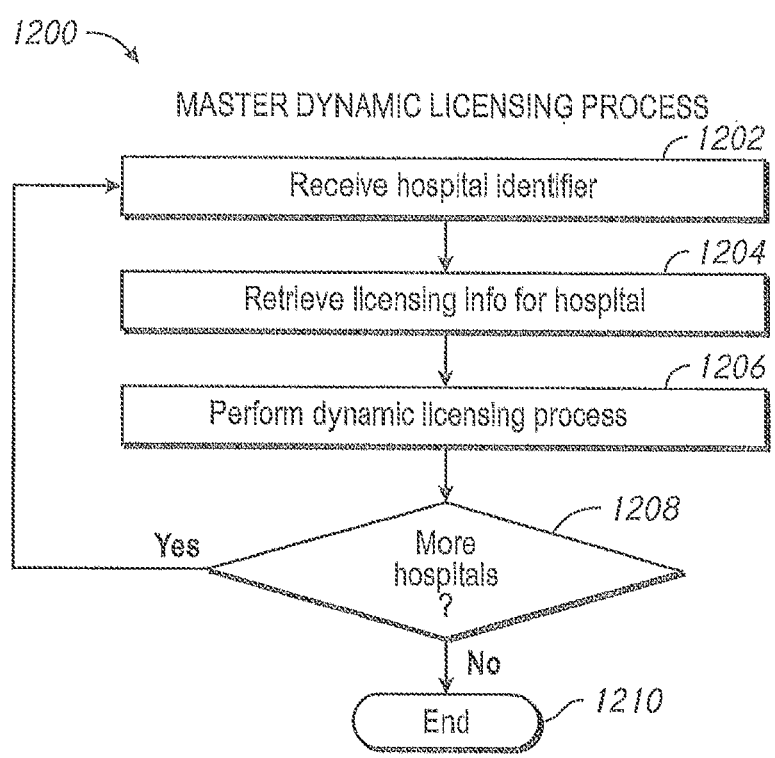
FIG. 12 is an exemplary flowchart showing a process for managing dynamic licenses for physiological parameters in multiple patient monitoring environments, according to certain embodiments.

FIG. 12 is a flowchart showing an exemplary master dynamic licensing process 1200 to manage dynamic licenses for physiological parameters for patient monitoring devices 110, 200, 300 and sensors 202 in multiple patient monitoring environments. At step 1202, the master dynamic licensing process 1200 receives a hospital identifier identifying the patient monitoring environment. At step 1204, the master dynamic licensing process 1200 retrieves licensing information associated and/or correlated with the identified hospital. At step 1206, the master dynamic licensing process 1200 performs a dynamic licensing process. In an embodiment, at step 1206, the master dynamic licensing process 1200 performs the dynamic licensing process 600 for a first hospital. At step 1208, the master dynamic licensing process 1200 determines if there are more hospitals or patient monitoring environments in which to manage dynamic licenses for physiological parameters for patient monitoring devices 110, 200, 300 and sensors 202. If there are additional hospitals or patient monitoring environments, the master dynamic licensing process 1200 returns to step 1202 and repeat steps 1204-1208. Otherwise, the master dynamic licensing process 1200 moves to end step 1210.

In another embodiment, the master dynamic licensing process 1200 is configured to monitor licenses for the sensors 202 patient monitoring devices 110, 200, 300 in at least a portion of the multiple patient monitoring environments and send information such as license start date, license stop date, and license duration to a billing program. In another example, the master dynamic licensing process 1200 keeps track of the pay-for use licenses and sends information such as the number of uses of a sensor and/or a patient monitoring device and/or license to a billing program. In another embodiment, the master dynamic licensing process 1200 generates the billing statements.

Figure 13:
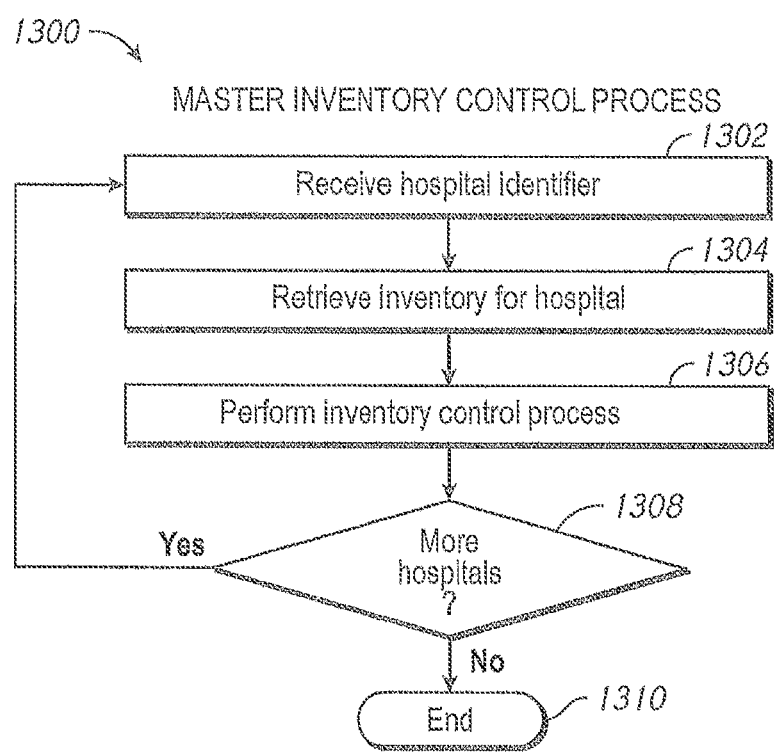
FIG. 13 is an exemplary flowchart showing an inventory control and auto-order process for patient monitoring equipment in multiple patient monitoring environments, according to certain embodiments.

FIG. 13 is a flowchart showing an exemplary master inventory control and auto-order process 1300 to control inventory and auto-order for patient monitoring devices 110, 200, 300 and sensors 202 in multiple patient monitoring environments. At step 1302, the master inventory control process 1300 receives a hospital identifier identifying the patient monitoring environment. At step 1304, the master inventory control process 1300 retrieves inventory information associated and/or correlated with the identified hospital. At step 1306, the master inventory control process 1300 performs an inventory control process. In an embodiment, at step 1306, the master inventory control process 1300 performs the inventory control process 700. At step 1308, the master inventory control process 1300 determines if there are more hospitals or patient monitoring environments in which to control inventory for patient monitoring devices 110, 200, 300 and sensors 202. If there are additional hospitals or patient monitoring environments, the master inventory control process 1300 returns to step 1302 and repeat steps 1304-1308. Otherwise, the master inventory control process 1300 moves to end step 1310.

Figure 14:
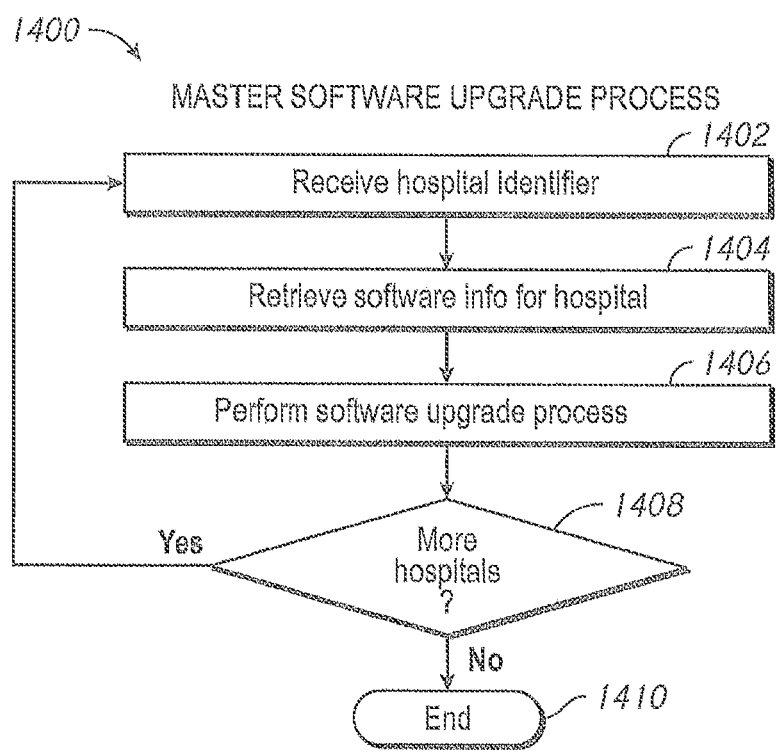
FIG. 14 is an exemplary flowchart showing a software version control process for patient monitoring equipment in multiple patient monitoring environments, according to certain embodiments.

FIG. 14 is a flowchart showing an exemplary master software version control process 1400 to upgrade software for patient monitoring devices 110, 200, 300 and sensors 202 in multiple patient monitoring environments. At step 1402, the master software version control process 1400 receives a hospital identifier identifying the patient monitoring environment. At step 1404, the master software version control process 1400 retrieves software information for the patient monitoring devices 110, 200, 300 and sensors 202 associated with the identified hospital. At step 1406, the master software version control process 1400 performs a software upgrade process. In an embodiment, at step 1406, the master software version control process 1400 performs the software upgrade process 800, 850. At step 1408, the master software version control process 1400 determines if there are more hospitals or patient monitoring environments in which to upgrade software for patient monitoring devices 110, 200, 300 and sensors 202. If there are additional hospitals or patient monitoring environments, the master software version control process 1400 returns to step 1402 and repeat steps 1404-1408. Otherwise, the master software version control process 1400 moves to end step 1410.

Figure 15:
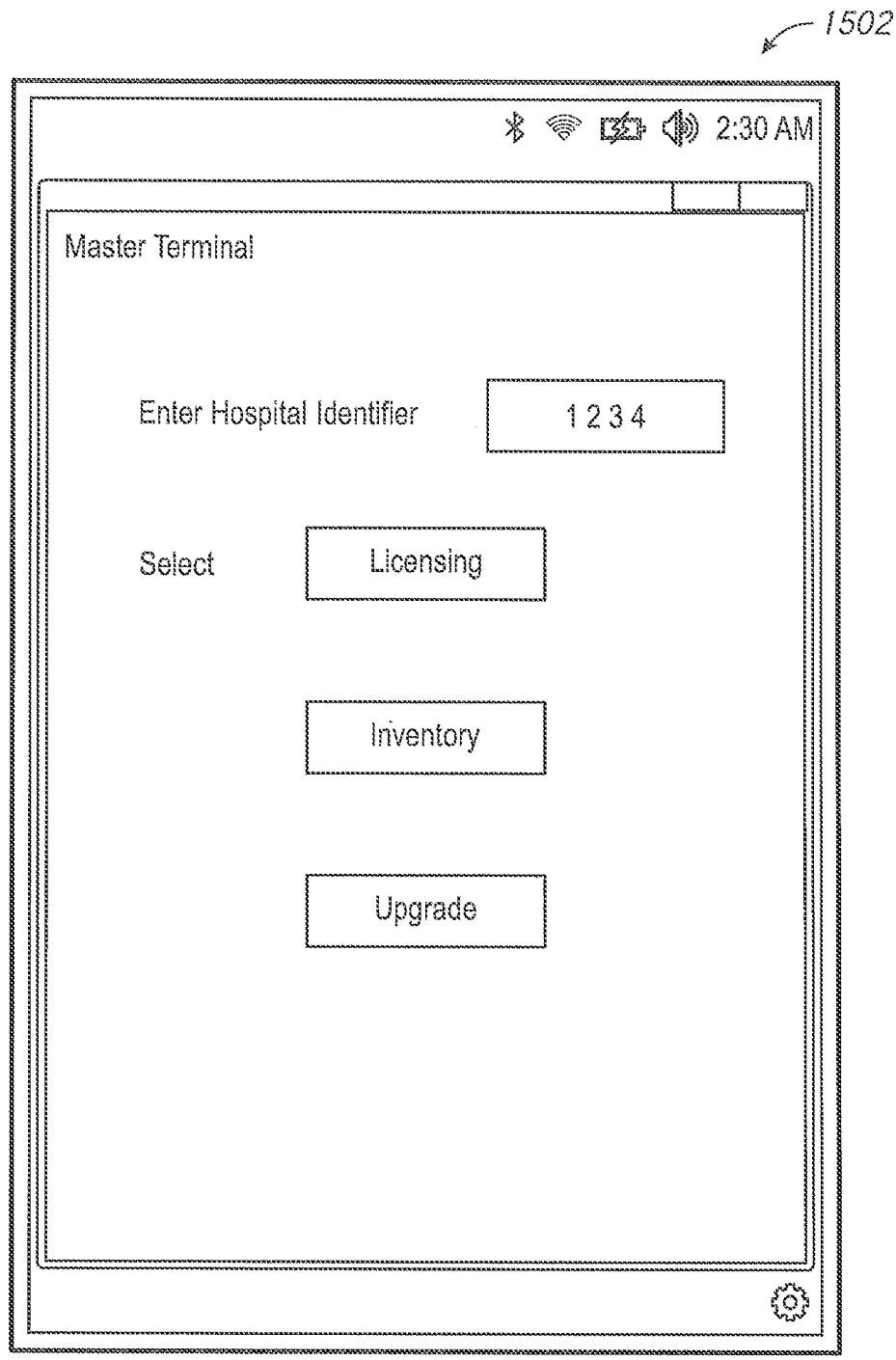
FIG. 15 is an exemplary screen shot illustrating access to the processes of FIGS. 12-14 from a master terminal, according to certain embodiments.

FIG. 15 is an exemplary screen shot illustrating access to the processes 1200, 1300, 1400 of FIGS. 12-14 from the master terminal 1142. In an embodiment, the user or administrator enters the hospital identifier and selects "licensing" to begin the master dynamic licensing process 1200, selects "inventory" to begin the master inventory control process 1300, or selects "upgrade" to begin the master software upgrade process 1400.

Dual Processors

Figure 16:
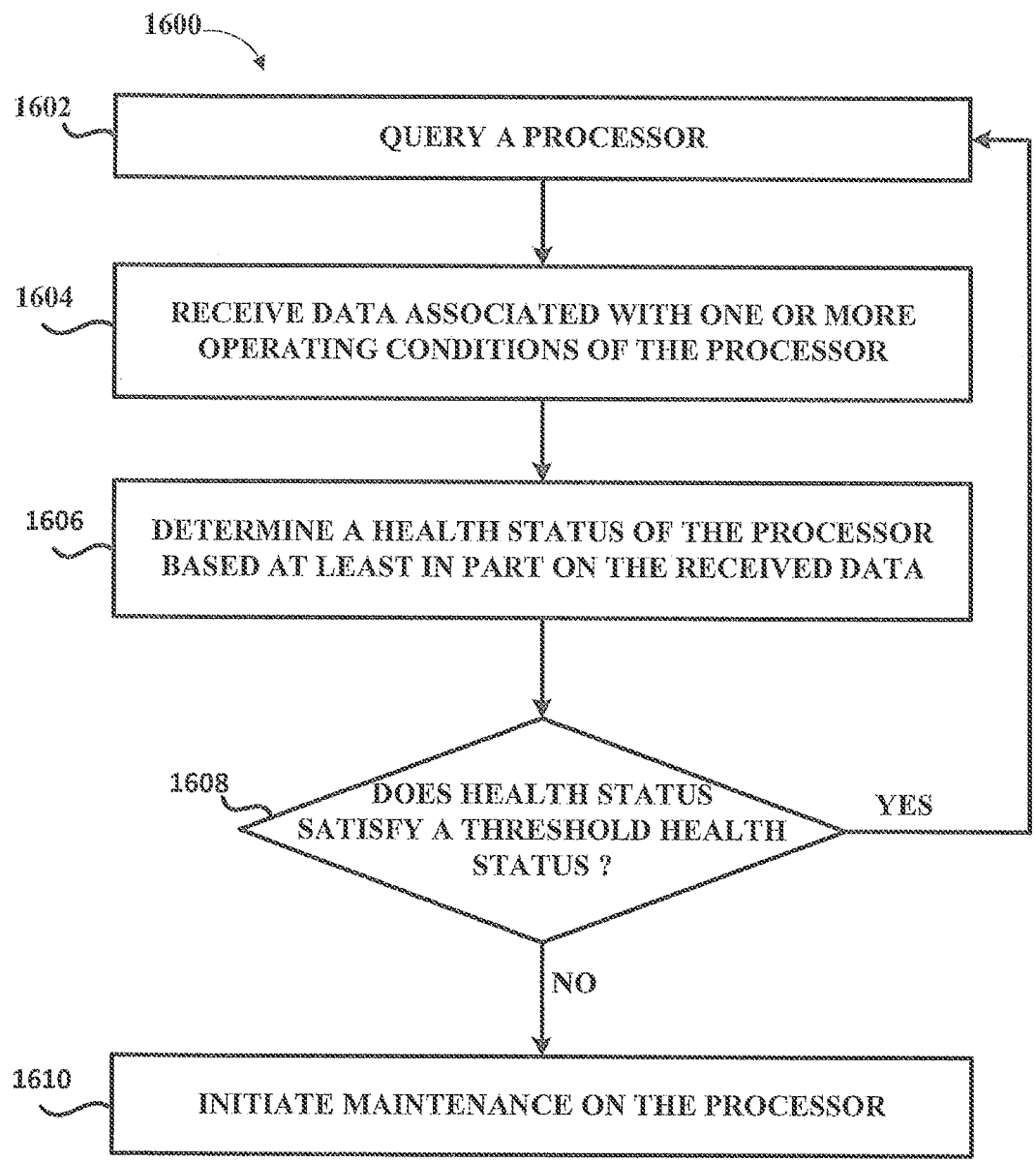
FIG. 16 is a flow diagram illustrative of an embodiment of a routine implemented by one or more processors of a patient monitoring system to ensure the processors in the system are running properly, according to certain embodiments.

FIG. 16 is a flow diagram illustrative of an embodiment of a routine implemented by one or more processors of a patient monitoring system to ensure the processors in the system are running properly. In some embodiments, the routine 1600 is implemented by at least two processors, where each respective processor ensures the other processor is running properly. Accordingly, in some embodiments, the patient monitoring system includes multiple processors which perform checks and maintenance on each other to ensure that at least one processor of the patient monitoring system is running properly. It will be understood that the various steps described herein with reference to FIG. 16 can be implemented in a variety of orders. For example, the patient monitoring system can implement some steps concurrently or change the order, as desired. Furthermore, it will be understood that fewer, more, or different steps can be used as part of the routine 1600. In addition, it will be understood that multiple processors of the patient monitoring system may be implementing the routine simultaneously or at overlapping or non-overlapping periods.

At step 1602, a first processor queries a second processor. The first and second processors can be separate and distinct from each other. In some embodiments, the query is a request for the second processor to send the first processor data which the first processor can use to determine whether the second processor is running properly. For instance, the query may include a request for the second processor to send the first processor a specific piece of information. In examples such as these, the first processor can determine whether the second processor is running correctly based at least in part on whether the first processor receives the correct information it requested via the query.

In response to receiving the query from the first processor, the second processor can generate a data signal indicative of one or more operating conditions of the second processor. For instance, the operating conditions of the second processor can include processor speed, percent of capacity usage of the processor, processor temperature, error logs, health status, etc. As one non-limiting example, the second processor may continuously or periodically determine an estimation of its own health status. Upon receipt of the query from the first processor, the second processor can transmit a signal indicative of the determined health status.

In some embodiments, the first processor does not query the second processor for information. Instead, the first processor can itself monitor certain aspects of the second processor. For instance, the first processor can monitor the temperatures and voltages of the second processor.

At step 1604, the first processor receives the data signal sent from the second processor. As mentioned above, the data signal can be indicative of one or more operative conditions of the second processor. For instance, the data signal can be associated and/or correlated with at least one of processor speed, processor temperature, voltages, error logs, or health status of the second processor.

At step 1606, the first processor determines a health status of the second processor. For instance, the first processor can determine the one or more operating conditions, and based on the one or more operating conditions, the first processor can determine a health status of the second processor. In some embodiments, the health status can be a percentage, such as on the scale of 0 to 100 percent. In other embodiments, the health status can have a binary range, such as 0 or 1, or can be one of a plurality of ranked categories such as "Great, "Good," "Ok," "Bad."

The determination of the health status can be based on whether the one or more operating parameters fall within a specific range or threshold. For example, a processor temperature at or below 60 degrees Celsius can be indicative of health status of 90%, 1, or Good. Likewise, a processor temperature at or above 100 degrees Celsius can be indicative of health status of 10%, 0, or Bad. As another example, the health status can be based on a percentage of capacity of the processor. If processor usage is around 100%, it can be indicative of the processor doing more work than it has the capacity for. Thus, if the processor is running at near 100%, it could indicate that the processor is not running properly or is performing too many tasks. Accordingly, a high percentage of capacity usage (e.g., above 90%) can be indicative of a low health status (e.g., 20%, 0, or Bad). It should be understood that the health status of the second processor can be determined based on an individual operating condition or a compilation of operating conditions. For instance, the health status can be based on a weighted aggregation of operating parameters.

At step 1608, the first processor determines whether the health status satisfies a threshold health status. As mentioned above, the threshold health status can be a specific percentage (for example, 75%, 80%, 85%, and 90%). Alternatively, the health status can satisfy a binary threshold (for example, 1 or 0) or the threshold health status can be satisfied if the health status is one of plurality of categories (e.g., "Great" or "Good"). In some embodiments, the first processor can also determine a health status of the second processor by monitoring temperatures and voltages of the second processor. If any of the temperatures or voltages are above a threshold, the first processor can initiate maintenance on the second processor (step 1610).

If the first processor determines that the second processor is healthy and running properly, the first processor can return to step 402 and restart the routine 1600. In some embodiments, the first processor continuously implements routine 1600. In other embodiments, the first processor periodically implements routine 1600 (e.g., every 30 sec, 1 min, 5 min, 30 min, 1 hr.).

At step 1610, if the health status does not satisfy the threshold health status, the first processor can initiate maintenance on the second processor. For instance, the first processor can perform some action which may adjust the health status of the second processor such that it satisfies the threshold health status. In some embodiments, the first processor restarts the second processor. In other embodiments, the first processor places the second processor in a "safe mode" or safe state.

As mentioned above, one or more additional processors can implement routine 1600. For instance, in some embodiments the second processor can implement the routine 1600 such that it is monitoring the first processor. Accordingly, the first and second processor would each be performing checks on the other. Alternatively, the second process can implement routine 1600 such that it is monitoring a third processor, which is separate and distinct from the first and second processors. In examples such as these, the third processor can implement routine 1600 such that it is monitoring the first processor. Accordingly, a circular monitoring process ensures, such that the first processor is monitoring the second processor, the second processor is monitoring the third processor, and the third processor is monitoring the first processor. It should be noted that any number of processors can be utilized in this manner. In addition, in some instances it may be advantageous for multiple processors to monitor the same processor. For example, in some embodiments, the second and third processor both monitor the first processor.

Each of the processors can have different functions and/or capabilities. For instance, the first processor can have higher capabilities that the second processor. As another example, the first processor can be an Application Processor System-on-Chip and the second processor can be a Supervisor microcontroller. In examples such as these, functionality of the patient monitoring device can be divided between the multiple processors. For instance, the Supervisor microcontroller can, among other things, control the boot up of the Application Processor as well as monitor the temperatures and voltages of the Application Processor. In addition, the Supervisor processor can also monitor "watchdog" messages from the Application Processor and can place the Application Processor in a safe state if communication fails. Similarly, Applications Processor software can monitor the Supervisor Processor. The Applications Processor can utilize extra capacity of the Supervisor Processor during operation. In addition, the Supervisor Processor can take over application operation from the Applications Processor at least temporarily while the Applications Processor reboots or is restored to health. In a situation when the Supervisor Processor takes over, it can operate a limited version of the application software or it can operate a full version.

Upgrading with Daughterboard

Figure 17:
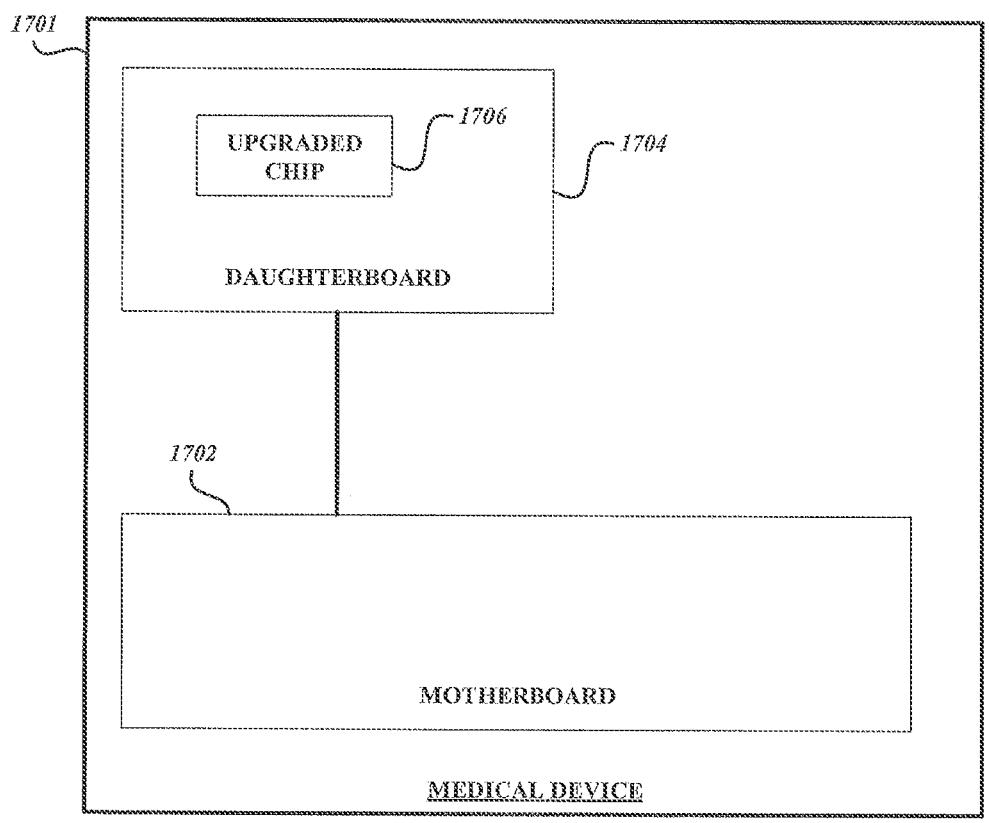
FIG. 17 is a diagram illustrative of an embodiment of a patient monitor, according to certain embodiments.

FIG. 17 is a diagram illustrative of an embodiment of a patient monitor. An important aspect of all medical device development includes obtaining medical device safety certifications. That is, evidencing that the safety certification has been performed in accordance with the appropriate safety standard. These certifications are extremely important in protecting the health and safety of patients, but come at the cost of delaying many completely safe medical devices and thereby delaying patients from receiving the best and most helpful patient care. Even if a medical device has received all of the required safety certifications, a minor hardware upgrade can necessitate re-certification. Accordingly, especially in fields which are constantly evolving, receiving these certifications can be a constant, time-intensive, expensive, tedious, process. For example, a wireless chipset is a constantly upgraded piece of hardware designed to allow a device to communicate with another wireless-enabled device. Wireless chipsets can be found in many medical devices and therefore pose a constant safety-recertification problem. Conventionally, a wireless chip set is soldered or otherwise connected to a motherboard. Consequently, the entire motherboard needs re-certification.

Accordingly, it is an aspect of the present disclosure to speed up the safety certification process by reducing what portions of the medical device need to be recertified. In some embodiments, the present physiological monitoring system advantageously simplifies the certification process by utilizing a daughterboard 1704 to upgrade the accessory of the medical device 1701. For purposes of this disclosure, a daughterboard 1704 can be a circuit board that plugs into, wireless communicates, solders onto, or otherwise connects to and extends the circuitry of the main processor board (e.g., motherboard 1702). By utilizing one or more daughterboards 1704 in addition to the motherboard 1702, the certification process can be simplified because, in some instances, only the daughterboard 1704 needs to be certified. Thus, the implementation of a daughterboard 1704 provides flexibility for interfacing with future devices without necessitating a complete re-certification of the motherboard 1702 of the medical device 1701.

Battery

Figure 18:
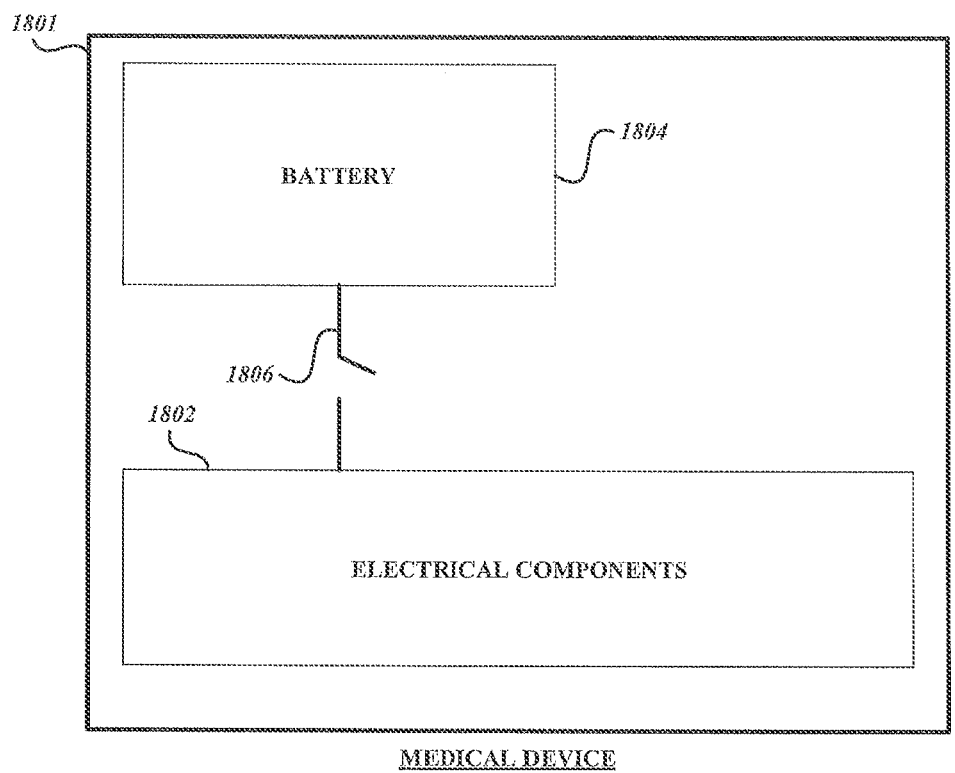
FIG. 18 is a diagram illustrative of an embodiment of a patient monitor, according to certain embodiments.

FIG. 18 is a diagram illustrative of an embodiment of a patient monitor. Battery management has become a key focus. Longer lasting and more reliable batteries not only provide increased convenience, but can also aid in providing better health care, for instance when the batteries are utilized in patient monitors. Batteries, such as Lithium-ion batteries, can offer extremely high energy density, making them ideal for use in portable device. The high energy density enables a small battery to provide a useful amount of power. However, batteries can be treacherous when fully charged, and if something causes the battery to fail in a way that releases this power quickly, the results can be personal injury or destruction of nearby electronics.

Accordingly, it is an object of the present disclosure to reduce the likelihood of a battery 1804 of a medical device 1801 discharging into and ruining electrical components 1802 of the medical device 1801. In particular, it is an object of the present disclosure to reduce the odds of a battery discharging into electrical components 1802 during shipping. Accordingly, in some embodiments, the battery 1804 can be disconnected from the medical device 1801 during shipping. This can reduce the likelihood of the battery 604 discharging into the electronics 1802 of the medical device 1801. In some embodiments, the battery 1804 may be physically separated from the medical device 1801. In alternative embodiments, the medical device 1801 may be set to a SHIPPING MODE which can electronically disconnect (for example, via a switch 1806) the battery 1804 from the medical device 1801. The medical device 1801 can be automatically or manually switched from the SHIPPING MODE to a USE MODE, which can re-connect the battery 1804 to the medical device 1801. In some embodiments, the medical device 1801 can switch to USE MODE automatically once the medical device 1801 is turned on.

In addition, overcharging or leaving a battery at full charge is a variable that can shorten the life of a battery. For instance, fully charging a battery can, for example, cause it to overheat which can result in a shorter lifespan. In some embodiments, a battery of a physiological monitoring device may have a life of approximately 350-500 charges. However, by not fully charging the battery, the battery can maintain a longer battery life. In addition, by continuously preventing the battery from reaching full charge, the battery life (in hours) can be generally maintained throughout the entire life of the battery (in charges). Accordingly, it is an object of the present disclosure to provide a battery which is not fully charged, for example, during shipment of the physiological monitoring device.

Recommended Care

Hospitals can be very stressful environments for the patients as well as the doctors and nurses. The nurses and doctors can be understaffed and overworked and can easily get caught up in a situation when some patients are checked on left often then they should be. While hospitals generally have systems in place which require or suggest a standard of care, for instance requiring a nurse to check on a patient every four hours, some patients require a much more frequent observation. Accordingly, it is an object of the present disclosure to provide a recommended care protocol (e.g., frequency of observations) based at least in part on the patient's current health status.

Figure 19:
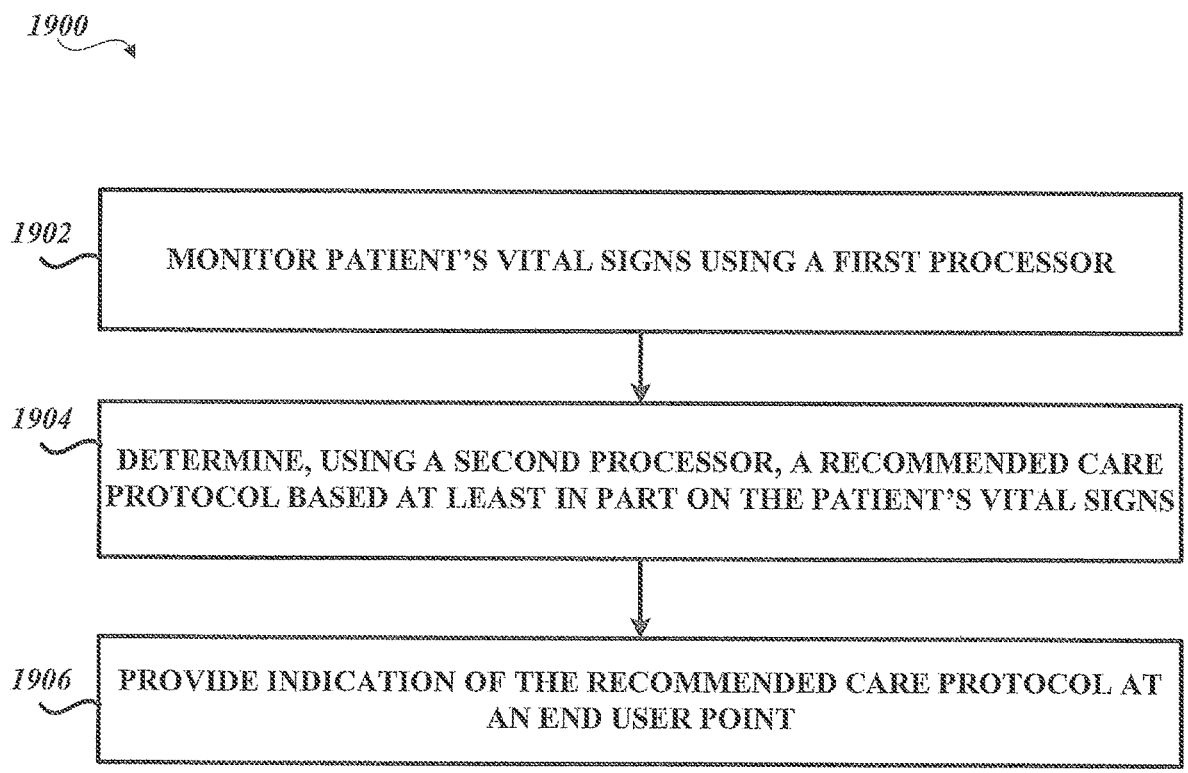
FIG. 19 is a flow diagram illustrative of an embodiment of a routine for providing a recommended care protocol, according to certain embodiments.

FIG. 19 is a flow diagram illustrative of an embodiment of a routine 1200 for providing a recommended care protocol. It will be understood that the various steps described herein with reference to FIG. 19 can be implemented in a variety of orders. For example, the patient monitoring system can implement some steps concurrently or change the order, as desired. Furthermore, it will be understood that fewer, more, or different steps can be used as part of the routine 1900.

At step 1902, the patient monitoring device monitors a patient's health status using a first processor. For instance, the first processor can monitor the patient's vital signs or other physiological parameters. In some embodiments, the first processor is an application processor or a supervisor processor, such as described with respect to FIG. 16.

At step 1904, a second processor determines a recommended care protocol based at least in part on the health status monitored by the first processor. In some embodiments, the first and second processors are the same processor. For instance, the second processor can be a separate application layer running on the first processor that does not affect the functions of the first processor. In some embodiments, the first and second processors are separate and distinct processors. For instance, it is important that the first processor accurately monitor the health status of the patient. Thus, the second processor can be separate and distinct from the first processor so that the first processor does not get bogged down determining a recommended care protocol.

The second processor can determine the recommended care protocol in a variety of ways. For instance, the second processor can receive the health status, vital signs, or physiological parameters from the first processor and use a predefined library to determine a recommended care protocol. For instance, the first processor determines that the blood pressure is very high (e.g., 160/100), then the second processor can use the library to look up a recommended care protocol for a very high blood pressure. In some instances, the recommended care protocol can suggest that a nurse visit a particular patient every 15, 30, or 45 min or every 1, 2, 3, 4, or 5+ hours. At step 1906, an indication of the recommended care protocol is provided at an end user point. For instance, the indication can be provided on a patient monitoring system, such as a Masimo ROOT® device, or at a nurses' station.

Hardware Encryption

Because medical device technology is constantly advancing, medical device providers, such as Masimo Corporation, are constantly developing new upgrades for their devices and systems. Thus, securely upgrading the medical device has become an item of concern. Providers want to provide upgrades to their devices but they want to limit unauthorized access to data and use of their equipment.

Software encryption programs can be used to protect devices within an organization, and these solutions can be cost effective as well as easy to use, upgrade and update. Software encryption can protect data at rest, in transit, and stored on different devices. Software-based encryption often includes additional security features that complement encryption, which cannot come directly from the hardware.

The protection granted by these solutions, however, is as strong as the level of security of the operating system of the device. A security flaw in the OS can easily compromise the security provided by the encryption code. Encryption software can also be complicated to configure for advanced use and, potentially, could be turned off by users. Performance degradation is a notable problem with this type of encryption.

Accordingly, it is an object of the present disclosure to provide a method of securely upgrading a system image of a device that uses hardware based encryption. Hardware-based encryption can use a device's on-board security to perform encryption and decryption. It can be self-contained and does not require the help of any additional software. Therefore, in some embodiments, it is free from the possibility of contamination, malicious code infection, or vulnerability.

Hardware encryption is tied to a particular device and one solution cannot be applied to the entire system and all its parts. Therefore, hardware-based encryption offers stronger resilience against attacks. In general, malicious hackers cannot apply brute-force attacks to a hardware-encrypted system as the crypto module can shut down the system and possibly compromise data after a certain number of password-cracking attempts.

Figure 20:
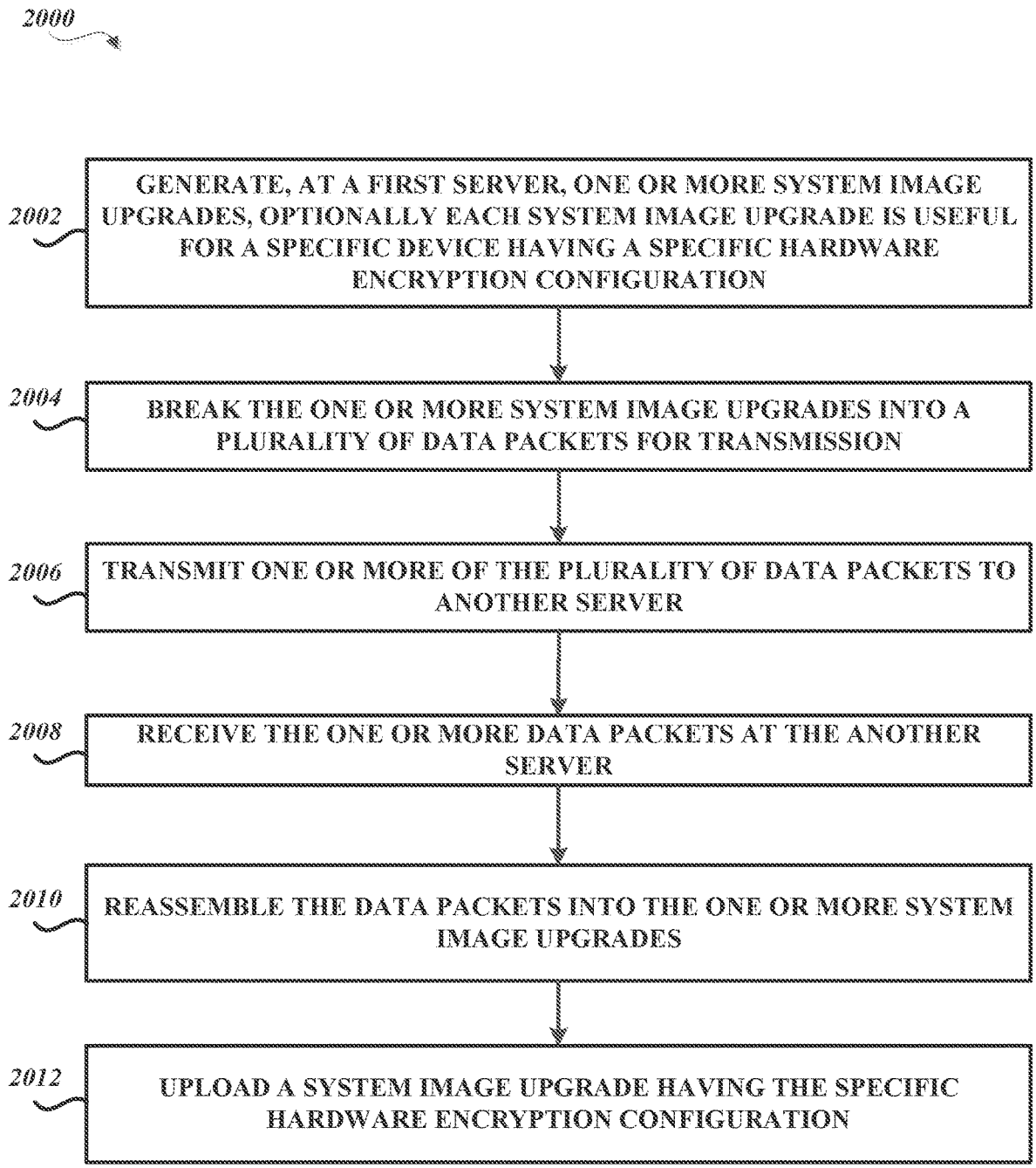
FIG. 20 is a flow diagram illustrative of an embodiment of a routine for securely upgrading a system image of a device by utilizing hardware based encryption, according to certain embodiments.

FIG. 20 is a flow diagram illustrative of an embodiment of a routine 2000 for securely upgrading a system image of a device by utilizing hardware based encryption. It will be understood that the various steps described herein with reference to FIG. 20 can be implemented in a variety of orders. For example, the patient monitoring system can implement some steps concurrently or change the order, as desired. Furthermore, it will be understood that fewer, more, or different steps can be used as part of the routine 2000.

At step 2002, one or more system image upgrades are generated, for instance, at a first server. Optionally, each system image upgrade is useful for a specific device having a specific hardware encryption configuration. As described above, because each device is encrypted at the hardware level, a particular system image upgrade may be useful for only one specific device having a particular hardware encryption configuration. Accordingly, in some embodiments, a different system image must be generated for each particular device. In other embodiments, more than one device can use the same system image upgrade.

At step 2004, the first server breaks the one or more system image upgrades into a plurality of data packets or unrelated files for transmission to the second server. In some embodiments, the system image upgrades can be further secured by encrypting the data packets. By separating the image into a plurality of data packets, no single or even small group of data packets is usable to determine the image. Moreover, groups of data packets are not usually transferred to the end destination of the exact same internet hops. Thus, it is further unlikely that a malicious hacker would be able to obtain all of the data packets to reassemble the image. Moreover, the data packets can be encrypted or scrambled such that only the end server is capable of reassembling the packets. At step 2006, the first server transmits one or more of the plurality of data packets to a second server, for instance a hospital server.

At step 2008, the second server receives the one or more data packets from the first server. At step 2010, the second server reassembles the data packets to generate the one or more system image upgrades. In some embodiments, the second server must decrypt the data packets before generating the one or more system image upgrades.

At step 2012, the second sever uploads a system image upgrade to a specific device having the required specific hardware configuration. In some embodiments, to provide further security, a system image upgrade cannot be installed a second time, even on the device with the correct hardware configuration. Instead, a new system image upgrade must be generated (step 2002). Advantageously, even if one or more of the system image upgrades are intercepted by a hacker, those upgrades only work on devices with specific hardware configurations. Thus, even if the upgrade were intended for a patient monitoring device of model A, the stolen system image upgrade would not be able to provide an upgrade to another monitoring device of model A because the another device does not have the specific hardware encryption configuration.

Because each device is encrypted at a hardware level, it can be costly to manufacture each of the devices. However, in some instances, the added security outweighs the additional costs.

Terminology

The embodiments disclosed herein are presented by way of examples only and not to limit the scope of the claims that follow. One of ordinary skill in the art will appreciate from the disclosure herein that many variations and modifications can be realized without departing from the scope of the present disclosure.

The term "and/or" herein has its broadest least limiting meaning which is the disclosure includes A alone, B alone, both A and B together, or A or B alternatively, but does not require both A and B or require one of A or one of B. As used herein, the phrase "at least one of A, B, and C" should be construed to mean a logical A or B or C, using a non-exclusive logical or.

The description herein is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. In a caregiver environment, a patient monitoring device comprising:
    at least one port configured to receive a signal from a physiological sensor that senses light after it has passed through the tissue of the patient, the signal indicative of at least one physiological parameter of the patient in response to the sensed light associated with the patient, wherein the signal is indicative of a monitoring event;
    one or more hardware processors in communication with the at least one port, the one or more hardware processors configured to determine one or more measurements of the at least one physiological parameter of the patient from the received signal; and
    memory comprising at least a data module, a previous image module that has been tested and a latest image module, the data module configured to store the one or more measurements of the at least one physiological parameter, each of the latest and previous image modules comprising a system image that includes executable instructions to at least determine the one or more measurements of the at least one physiological parameter of the patient from the received signal;
    the one or more hardware processors in communication with the memory and further configured to:
        determine a state of an override;
        boot from the latest image module, wherein booting from the latest image module occurs during active monitoring when the override is enabled and occurs during a time of non-monitoring when the override is disabled.

2. The patient monitoring device of claim 1 wherein a system image associated with the latest image module has a later timestamp that a system image associated with the previous image module.

3. The patient monitoring device of claim 1 wherein the one or more processors are further configured to determine whether the one or more hardware processors are operating successfully after booting from the latest image module.

4. The patient monitoring device of claim 3 wherein the one or more processors are further configured to determine whether the one or more hardware processors are operating successfully after booting from the latest image module by performing a self-check.

5. The patient monitoring device of claim 3 wherein the one or more processors are further configured to boot from the previous image module when the one or more hardware processors are not operating successfully after booting from the latest image module.

6. The patient monitoring device of claim 3 wherein the one or more processors are further configured to repair the latest image module when the one or more hardware processors are not operating successfully after booting from the latest image module.

7. The patient monitoring device of claim 1 wherein the one or more processors are further configured to determine whether an image upgrade is available.

8. The patient monitoring device of claim 7 wherein the one or more processors are further configured to download the image upgrade to the previous image module responsive to a determination that the one or more hardware processors are operating successfully after booting from the latest image module.

9. The patient monitoring device of claim 7 wherein the one or more processors are further configured to download the image upgrade to the latest image module responsive to a determination that the one or more hardware processors are not operating successfully after booting from the latest image module.

10. The patient monitoring device of claim 9 wherein the one or more processors are configured to download the image upgrade from the Internet.

11. A method to upgrade operation of a patient monitoring device that is used in a caregiver environment, the patient monitoring device configured to communicate with a physiological sensor that senses light after it has passed through the tissue of a patient and generates a signal indicative of at least one physiological parameter of the patient in response to the sensed light associated with the patient, the patient monitoring device further configured to receive the signal and determine one or more measurements of the at least one physiological parameter of the patient from the received signal, the method comprising:
storing in memory comprising a data module the one or more measurements of the at least one physiological parameter, the memory further comprising at least a previous image module that has been tested and a latest image module, each of the latest and previous image modules comprising a system image that includes executable instructions to at least determine the one or more measurements of the at least one physiological parameter of the patient from the received signal;
determining a state of an override;
booting from the latest image module, wherein booting from the latest image module occurs during active monitoring when the override is enabled and occurs during a time of non-monitoring when the override is disabled.

12. The method of claim 11 wherein a system image associated with the latest image module has a later timestamp that a system image associated with the previous image module.

13. The method of claim 11 further comprising determining whether one or more hardware processors are operating successfully after booting from the latest image module.

14. The method of claim 13 further comprising determining whether the one or more hardware processors are operating successfully after booting from the latest image module by performing a self-check.

15. The method of claim 13 further comprising booting from the previous image module when the one or more hardware processors are not operating successfully after booting from the latest image module.

16. The method of claim 13 further comprising repairing the latest image module when the one or more hardware processors are not operating successfully after booting from the latest image module.

17. The method of claim 11 further comprising determining whether an image upgrade is available.

18. The method of claim 17 further comprising downloading the image upgrade to the previous image module responsive to a determination that one or more hardware processors are operating successfully after booting from the latest image module.

19. The method of claim 17 further comprising downloading the image upgrade to the latest image module responsive to a determination that one or more hardware processors are not operating successfully after booting from the latest image module.

20. The method of claim 19 further comprising downloading the image upgrade from the Internet.

* * * * *